United States Patent
Yue et al.

(10) Patent No.: US 9,717,737 B2
(45) Date of Patent: Aug. 1, 2017

(54) VACUOLIN-1 AS AN INHIBITOR OF AUTOPHAGY AND ENDOSOMAL TRAFFICKING AND THE USE THEREOF FOR INHIBITING TUMOR PROGRESSION

(71) Applicant: The University of Hong Kong, Hong Kong (CN)

(72) Inventors: Jianbo Yue, Hong Kong (CN); Yingying Lu, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 15/039,744

(22) PCT Filed: Feb. 25, 2015

(86) PCT No.: PCT/CN2015/073255
§ 371 (c)(1),
(2) Date: May 26, 2016

(87) PCT Pub. No.: WO2015/124120
PCT Pub. Date: Aug. 27, 2015

(65) Prior Publication Data
US 2016/0375029 A1    Dec. 29, 2016

Related U.S. Application Data

(60) Provisional application No. 61/941,693, filed on Feb. 19, 2014.

(51) Int. Cl.
*A61K 31/535* (2006.01)
*A61K 31/5377* (2006.01)
*A61K 31/337* (2006.01)
*A61K 31/436* (2006.01)
*A61K 31/513* (2006.01)

(52) U.S. Cl.
CPC ........ *A61K 31/5377* (2013.01); *A61K 31/337* (2013.01); *A61K 31/436* (2013.01); *A61K 31/513* (2013.01)

(58) Field of Classification Search
CPC .................................................. A61K 31/5377
USPC ....................................................... 514/236.2
See application file for complete search history.

(56) References Cited

U.S. PATENT DOCUMENTS

2006/0019951 A1*   1/2006   Kirchhausen ........ C07D 251/70
                                                           514/235.5

OTHER PUBLICATIONS

Lu et al. Autophagy 10:11, 1895-1905; Nov. 2014.*
Sano et al. FEBS Letters 590 (2016) 1576-1585 , 2016.*
International Search Report in International Application No. PCT/CN2015/073255, filed Feb. 25, 2015.

* cited by examiner

*Primary Examiner* — Nizal Chandrakumar
(74) *Attorney, Agent, or Firm* — Saliwanchik, Lloyd & Eisenschenk

(57) ABSTRACT

Methods of treating autophagy related diseases, e.g. cancer and malaria, using novel autophagy inhibiting agents are described.

4 Claims, 25 Drawing Sheets

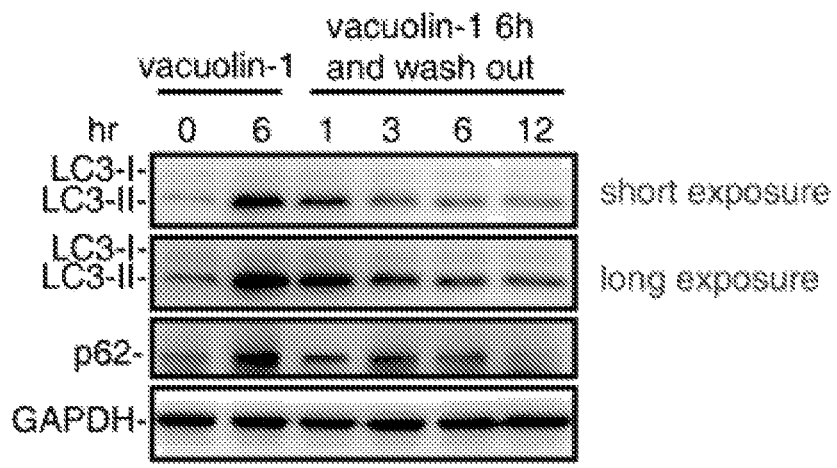
Figure 4C
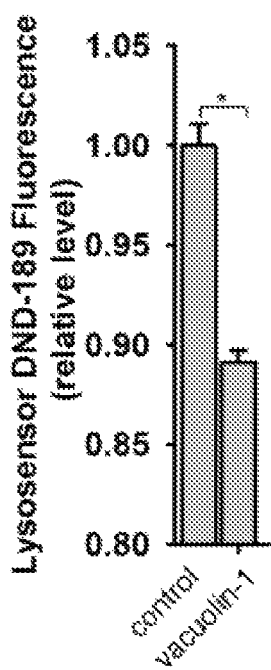 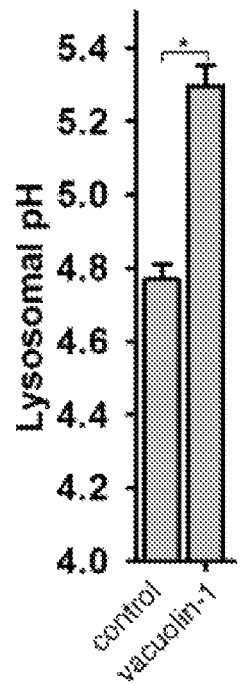
Figure 4D       Figure 4E

VACUOLIN-1 AS AN INHIBITOR OF AUTOPHAGY AND ENDOSOMAL TRAFFICKING AND THE USE THEREOF FOR INHIBITING TUMOR PROGRESSION

CROSS-REFERENCE TO RELATED APPLICATIONS

This application is the U.S. national stage application of International Patent Application No. PCT/CN2015/073255, filed Feb. 25, 2015, which claims the benefit of U.S. Provisional Patent Application No. 61/941,693, filed Feb. 19, 2014.

FIELD OF THE INVENTION

The present invention relates generally to the field of compositions and methods for treatment of autophagy related human diseases. More particularly, the present invention provides methods of using small chemicals to manipulate autophagy and to treat autophagy related human diseases, e.g. cancer.

BACKGROUND

Autophagy is an evolutionarily conserved catabolic degradation cellular process in which misfolded proteins or damaged organelles are first sequestered by a double-membrane vesicle, called autophagosomes. Autophagosomes are then fused with lysosomes to digest and recycle the contents to maintain cellular homeostasis. Autophagy can also be markedly induced by a wide variety of stresses, e.g. nutrient starvation, infection, and aging, for cell survival. Dysfunctional autophagy has been associated with wide ranges of human diseases, such as, e.g., cancer, neurodegenerative diseases, heart disease, diabetes, and bacterial infection (Wirawan et al., 2012; Yang and Klionsky, 2010).

Autophagy is a double-edged sword for many cellular processes, depending upon the genetic background and microenvironment. For example, autophagy can act as a tumor suppressor by preventing oncogenic protein substrates, toxic misfolded proteins, damaged organelles, and reactive oxygen species (ROS) from accumulating to cause genome instability and cancer initiation (Mathew et al., 2009; Yue et al., 2003). On the other hand, higher basal autophagic activity detected in established tumor cells functions to promote the survival and growth of tumors by maintaining energy production under increased metabolic consumption and a hypoxic microenvironment, thereby enabling tumors to escape chemotherapy and/or radiation (Amaravadi et al., 2007; Lock et al., 2011; Lum et al., 2005; Yang et al., 2011). Therefore, dissecting the molecular mechanisms in regulating autophagy and identifying specific autophagy inhibitors or inducers suitable for clinical application are necessary for specifically targeting autophagy to fight human disease.

A large number of chemicals have been found to either promote or inhibit autophagy. Some of these compounds have been widely used to dissect the mechanisms underlying autophagy (Baek et al., 2012). Popular autophagy inducers include mTOR kinase inhibitors, e.g., rapamycin and torin 1 (Hanson et al., 2013), and chemicals inhibiting inositol monophosphatase, e.g., lithium and carbamazepine (Hidvegi et al., 2010). Notably, rapamycin is an immunosuppressant and has recently been used as an anticancer agent (Ravikumar et al., 2004). Lithium has also been used to treat Huntington's disease and other related neurodegenerative disorders (Sarkar et al., 2005). Commonly used autophagy inhibitors include chloroquine (CQ), 3-methyladenine, wortmannin, and bafilomycin (BAF) (Baek et al., 2012; Rote and Rechsteiner, 1983; Seglen and Gordon, 1982; Wu et al., 2013). Since established tumor cells normally activate autophagy to escape chemotherapy and/or radiation (Yang et al., 2011), numerous preclinical studies found that inhibition of autophagy by CQ restored chemosensitivity and promoted tumor cell death by diverse anticancer therapies (Kimura et al., 2013). Although CQ offers great promise for cancer therapy, CQ induces ocular toxicities and damages the renal system, and it is uncertain whether the tolerated doses of HCQ or CQ can be reached in human tumors to effectively inhibit autophagy (Kimura et al., 2013). Moreover, most of the available autophagy inhibitors, like HCQ or CQ, also lack either specificity, potency, or antitumor activity (Janku et al., 2011). Thus, potent and specific inhibitors of autophagy are needed in order to provide a novel and powerful approach for future cancer therapy.

Recently, many new autophagy chemical modulators have been identified either by screens based on clearance of aggregates of mutant a-synuclein in cells or by image-based screens with GFP-LC3 transfected cells. Although these small chemicals are useful pharmacological tools to study autophagy and are potential therapeutic drugs for autophagy-related diseases, many of these compounds still lack either specificity or potency, or both (Rubinsztein et al., 2012). Therefore, the search for specific and potent autophagy chemical modulators must continue in order to gain deep insight into autophagy and provide potential therapeutic drugs.

By screening a Chembridge library (ChemBridge Corporation, San Diego) that contains around 10,000 drug-like or lead-like small chemicals, vacuolin-1 was originally found to induce homotypic fusion of endosomes or lysosomes, thereby forming large vacuoles. Yet, it does not alter other cell structures and membrane trafficking functions (Cerny et al., 2004; Huynh and Andrews, 2005; Shaik et al., 2009). It remains controversial whether vacuolin-1 blocks the $Ca^{2+}$-dependent exocytosis of lysosomes.

BRIEF SUMMARY

The present invention provides methods of using vacuolin-1 and its analogues to manipulate autophagy and to treat autophagy related human diseases, e.g. cancer. The present invention also provides application of vacuolin-1 and its analogues for inhibiting autophagy and endosomal trafficking.

In one aspect, methods for treatment of cancer, such as, but not limited to, lung carcinoma and nasopharyngeal carcinoma are provided. The methods comprise administering a therapeutically effective amount of vacuolin-1, and/or one or more analogues, alone or in combination with one or more chemotherapy drugs to a subject who has cancer. In at least one embodiment, the methods are used to treat cancers that are susceptible to treatment with an autophagy inhibiting agent.

In some embodiments, the methods result in inhibition of autophagy and/or endosomal traffic. In some embodiments, the methods result in activation of Rab5, which leads to maturation of endosomes and lysosomes and contributes to lysosomal pH increase. In some embodiments, the chemotherapy drugs can include taxol, 5-Fu, temirolimus, and combinations thereof.

In other aspects of the invention, vacuolin-1 analogues are identified by virtual screening.

DETAILED DESCRIPTION

The present invention describes vacuolin-1 and its analogues as potent and reversible inhibitors of autophagy and endosomal traffic and methods of using vacuolin-1 and its analogues alone or in combination with chemotherapeutic drugs, e.g. 5-FU, temsirolimus, and taxol, or alone, to manipulate autophagy and to treat cancer, e.g. prostate, breast, and nasopharyngeal carcinoma, or malaria, respectively.

In one aspect, methods for treatment of cancer, such as but not limited to, colon carcinoma, prostate cancer, breast cancer, osteosarcoma and/or nasopharyngeal carcinoma, are provided. The methods comprise administering a therapeutically effective amount of vacuolin-1, and/or one or more analogues, either alone or in combination with one or more chemotherapy drugs to a subject who has cancer.

In another aspect, methods for treatment of malaria are provided. The methods comprise administering a therapeutically effective amount of vacuolin-1, and/or one or more analogues, to a subject who is infected with malaria.

In some embodiments, the methods result in inhibition of autophagy and/or endosomal traffic. In some embodiments, the methods result in activation of Rab5, which leads to maturation of endosomes and lysosomes and contributes to lysosomal pH increase. In some embodiments, the chemotherapy drugs can include, but are not limited to, taxol, 5-Fu, temirolimus, and combinations thereof.

In other aspects of the invention, additional vacuolin-1 analogues are identified by virtual screening.

Figure 1:
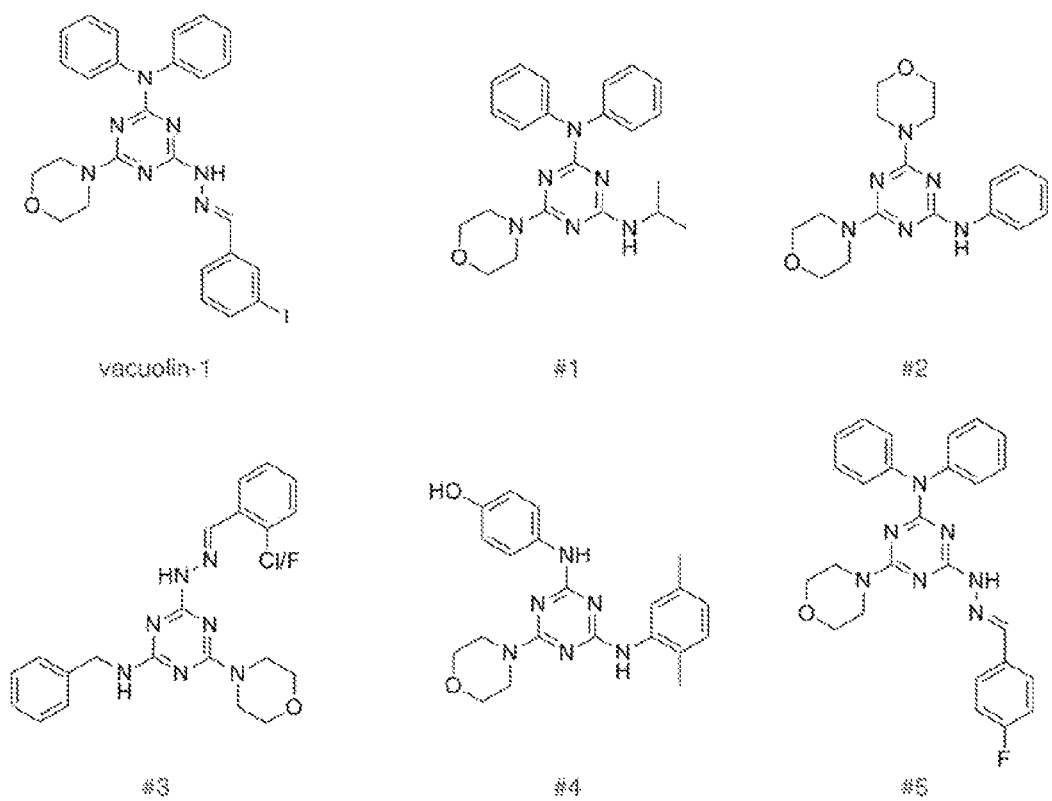
FIG. 1 shows structures of vacuolin-1 and structural analogues.
Figure 4A:
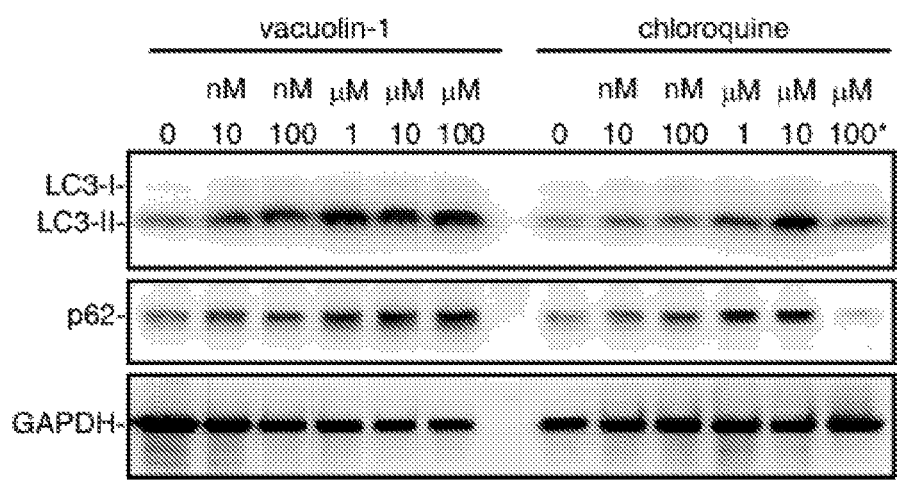
FIG. 4 shows (A) western blot analyses of LC3 and p62 in HeLa cells following treatment with vacuolin-1 or CQ at the indicated dose for 6 hours; (B) an MTT assay for cell viability in HeLa cells treated with vacuolin-1 or CQ for the indicated doses for 48 hours; (C) western blot analyses of LC3 and p62 in vacuolin-1 (1 μM) treated HeLa cells; (D) microplate reader measurement of Lysosensor DND-189 stained HeLa cells following vacuolin-1 (1 μM) induction; (E) microplate reader measurement of quantitative ratiometric LysoSensor Yellow/Blue DND-160 stained HeLa cells following vacuolin-1 (1 μM) induction; and (F) Fura-2 loaded HeLa cells following vacuolin-1 (1 μM) pretreatment for 5 hours followed by GPN (200 μM) induced lysosomal $Ca^{2+}$ release.
Figure 4B:
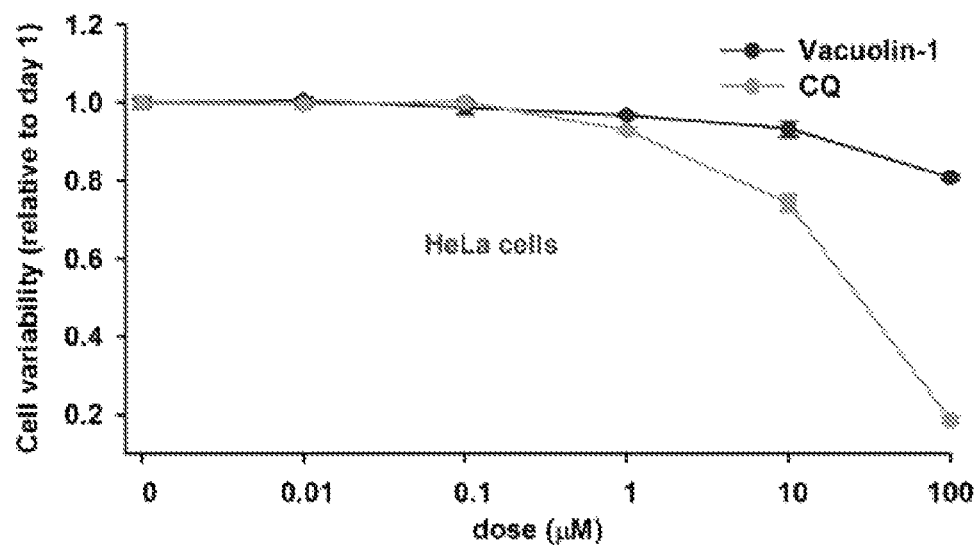
Figure 4F:
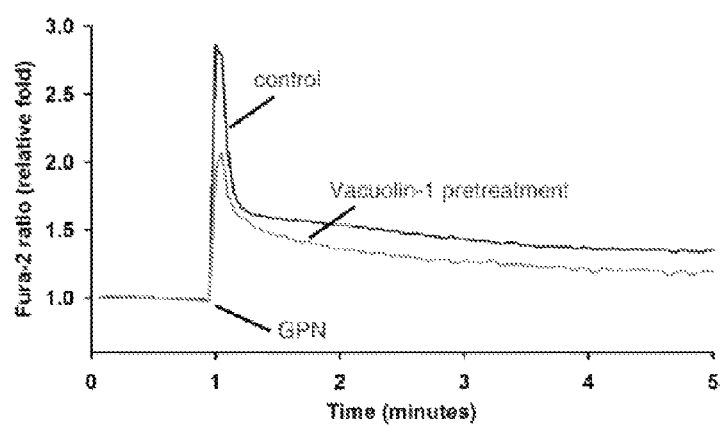
Figure 4F:
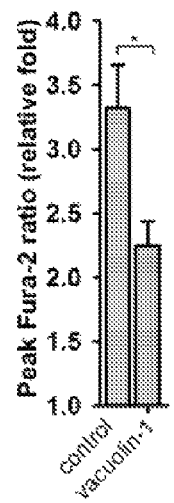
Figure 5:
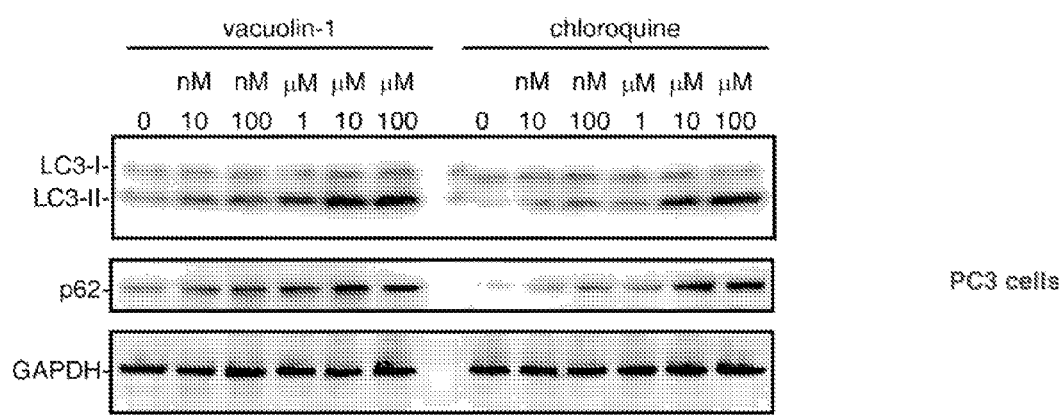
FIG. 5 shows western blot analyses against LC3 and p62 in PC3 prostate cancer cells treated with vacuolin-1 or CQ at indicated dose for 6 hours.

The small chemical, vacuolin-1, and its analogues (FIG. 1) potently and reversibly inhibit autophagy by blocking the fusion between autophagosomes and lysosomes in mammalian cells, thereby leading to the accumulation of autophagosomes (FIGS. 2-5, and 12). Vacuolins are less toxic than chloroquine (CQ) but are at least 10 folds more potent in inhibiting autophagy as compared to CQ (FIGS. 3-5). Vacuolin-1 and its analogues present a novel class of drug that can potently and reversibly modulate autophagy.

The present invention describes vacuolins as potent inhibitors of general endosomal traffic (FIG. 7) and a novel class of Rab5 GTPase activators (FIG. 8).

Furthermore, methods to treat human cancers, e.g. colon carcinoma, osteosarcoma, and nasopharyngeal carcinoma, with vacuolins in combination with other chemotherapy drugs, e.g. 5-FU, temsirolimus, and taxol (FIGS. 13 and 14) are provided herein. It is also contemplated that vacuolins, and/or analogs thereof, can be utilized alone in the treatment of cancers. Furthermore, the present invention also provides methods to treat malaria with vacuolins (FIG. 15).

Figure 13:
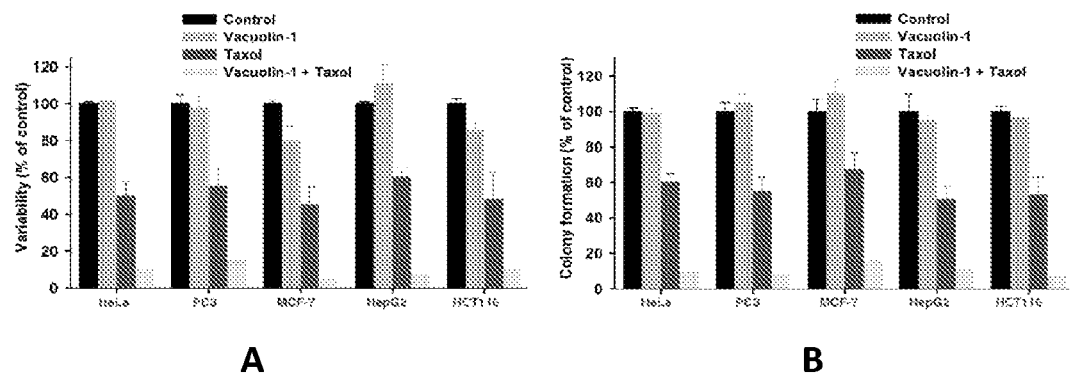
FIG. 13 shows vacuolin-1 potently enhances the anti-tumor effects of chemotherapy drugs in human cancer cell lines. (A) Vacuolin-1 augments the anti-tumor effects of chemotherapy drugs (B) Vacuolin-1 in combination with chemotherapy drugs greatly decreases the colony formation efficiency cancer cells.
Figure 14:
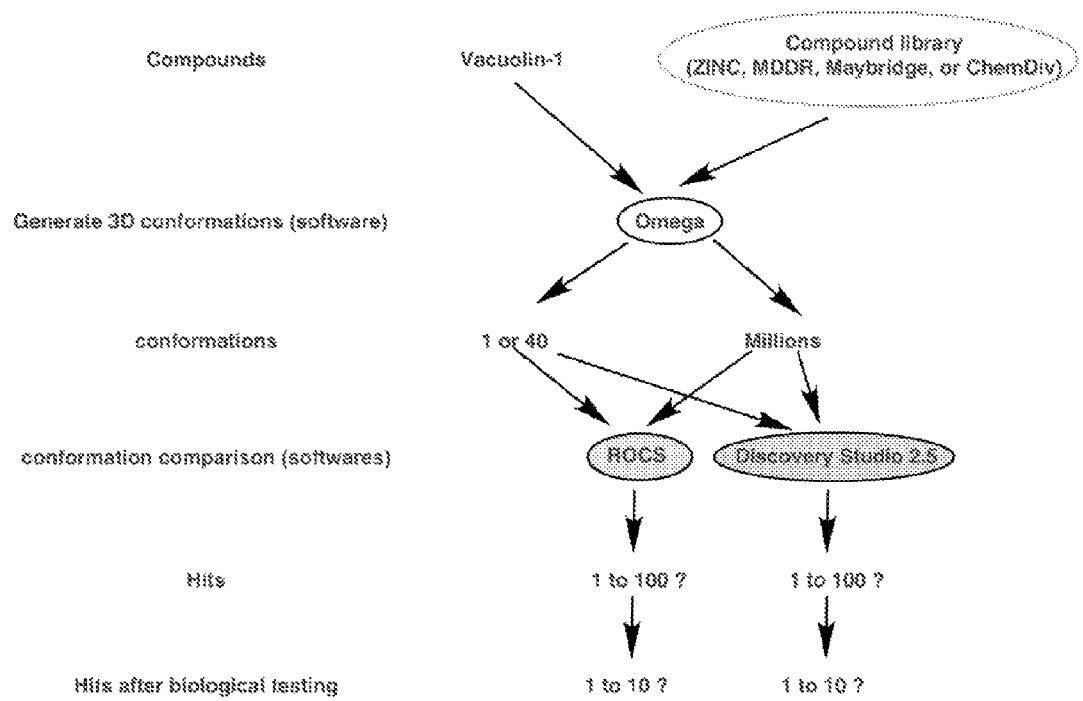
FIG. 14 shows a virtual screening strategy for vacuolin-1 analogue identification using ChemDiv.
Figure 15:
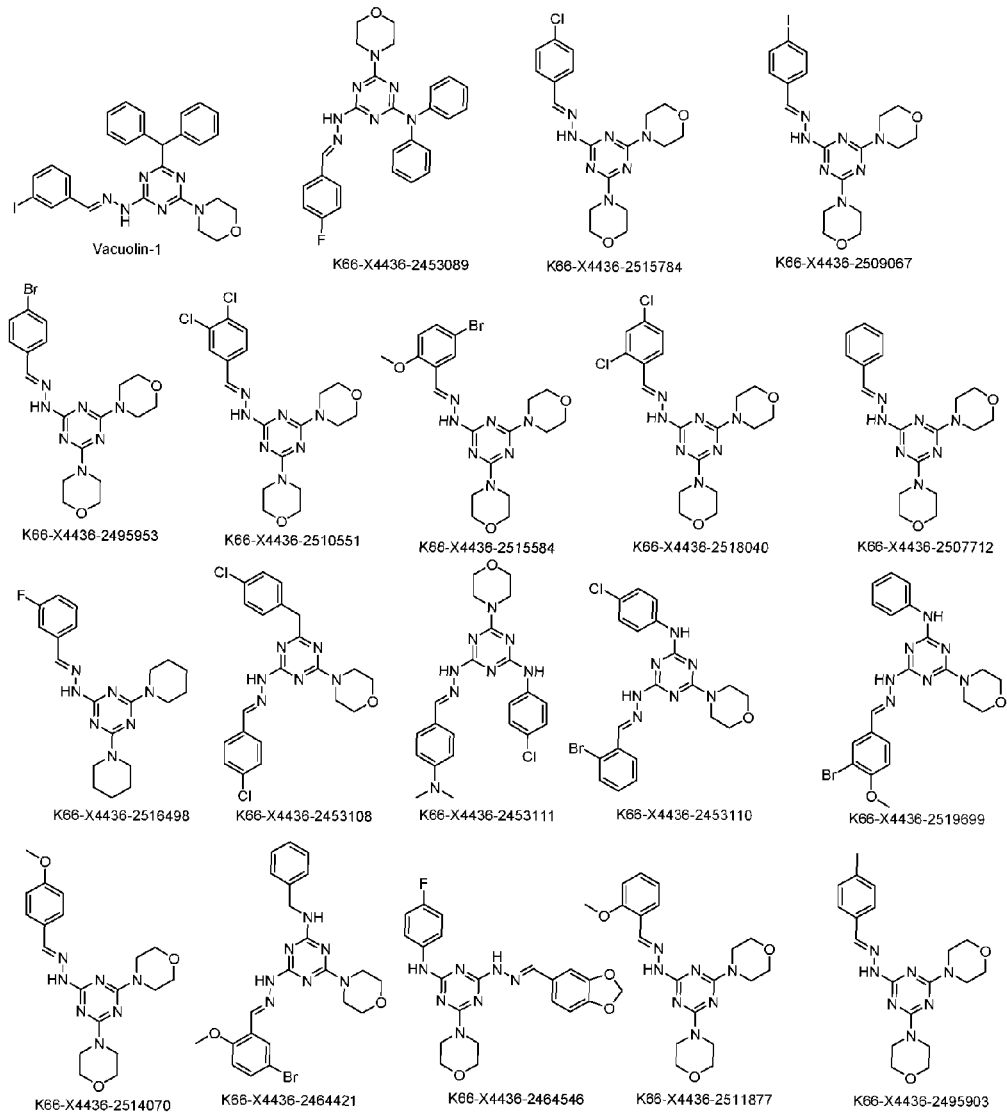
FIG. 15 shows vacuolin-1 analogues.

In at least one aspect, vacuolins are used in combination with chemotherapeutic drugs, e.g. 5-FU, temsirolimus, and taxol, to synergistically kill a panel of tumor cell lines in vitro and suppress tumor growth in xenograft mouse models (FIGS. 13 and 14). It is expected that vacuolin-1 and its analogues provide a novel therapeutic strategy for fighting cancers. It is also expected that vacuolins sensitize tumor cells carrying wild type p53, not mutant p53, to chemotherapeutic drugs.

Figure 6:
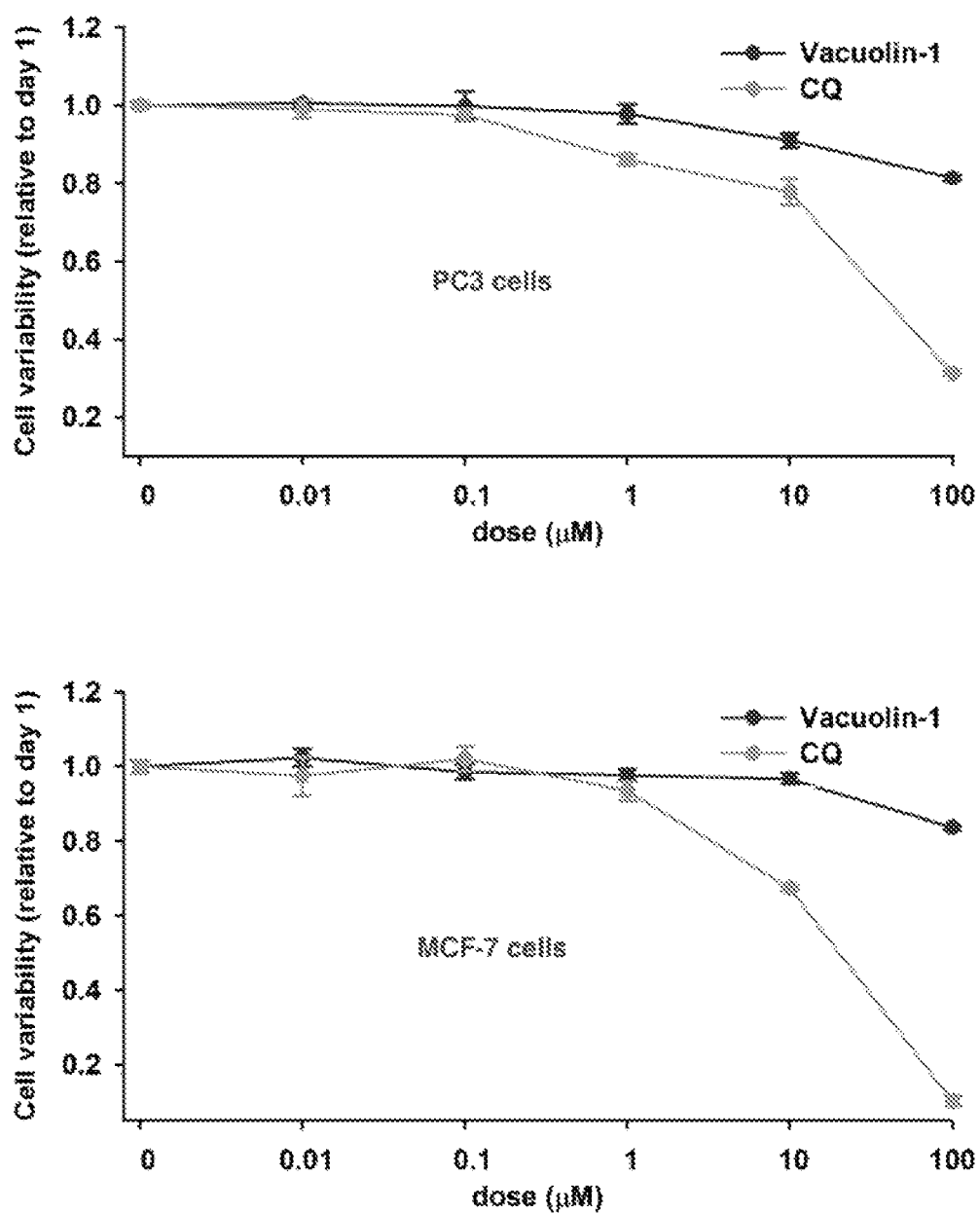
FIG. 6 shows line graphs of cell viability measured by MTT assays for PC3, HepG2, MCF7, and A549 cells treated with vacuolin-1 or CQ for the indicated doses for 48 hours.
Figure 6:
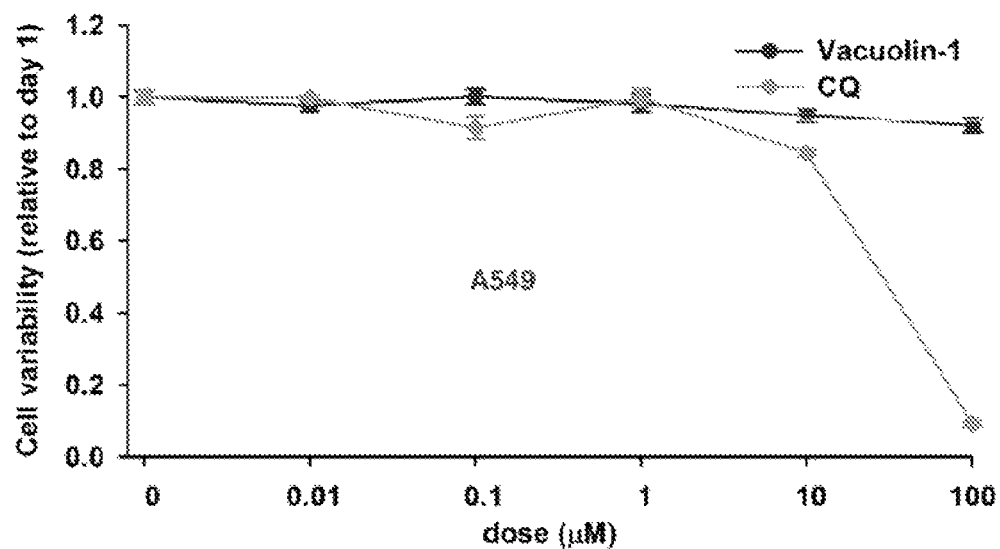
Figure 6:
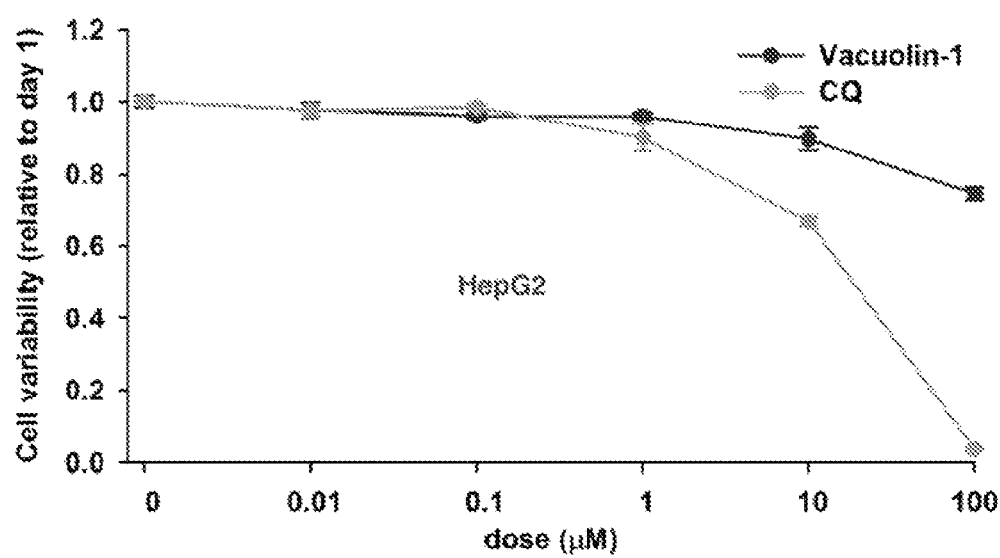

Vacuolins are cell-permeable and water soluble triazine based compounds. Compared to other popular autophagy modulators, such as CQ which has been applied in a dozen anti-cancer clinical trials, vacuolins are at least 10 fold more potent in inhibiting autophagy while exhibiting little toxicity in a wide variety of cancer cell lines (FIGS. 4 and 6). Besides inhibiting autophagy, vacuolins potently and reversibly inhibit endosomal traffic as well (FIG. 7).

Vacuolins markedly activate Rab5 and expression of Rab5A-DN or Rab5A knockdown abolishes vacuolin-1 mediated autophagy inhibition (FIG. 8). Rab5 is a master regulator for the biogenesis of the endolysosomal system, and no drugs, other than vacuolins, are found to modulate its activity thus far. Therefore, vacuolins are the first class of Rab5 agonists to be identified and can be widely used in basic research related to both autophagy and intracellular traffic.

Vacuolins also modestly inhibit V-ATPase activity (30% at 1 µM), which may be due to the fact that V-ATPase is sensitive to hydrophobic compounds in general (FIG. 8). Thus, vacuolins are not specific V-ATPase inhibitors, but nonetheless at least partially lead to the increase of lysosomal pH, which may also contribute to autophagy inhibition. In addition, endosomal traffic is essential for the function and biogenesis of lysosome because lysosomes depend on the influx of new components. Without incoming endosomal traffic, lysosomes lose their intact morphology, contents of protons and other ions, and perinuclear localization (Huotari and Helenius, 2011; Spang, 2009). Thus, vacuolins constitutively activate Rab-5, and active Rab5 stops endosome maturation, which subsequently compromises the biogenesis and function of lysosomes. This should also partially contribute to the increase of lysosomal pH.

The present invention also provides toxicity studies of the vacuolins in combination with, or without, chemotherapy drugs in both tumor-free and tumor-bearing mice. Since vacuolins are much less toxic than CQ and its effects on cells are reversible, the toxicity of vacuolins on mice is much less than CQ.

The present invention further provides pharmacokinetic studies on vacuolins in normal mice or rats. The blood concentration of vacuolins after the intragastric (oral), intravenous, intramuscular, or subcutaneous administration is determined. In addition, the metabolites of vacuolins after incubating vacuolins with liver microsomes are determined. Compared to CQ, which exhibits high toxicity alone and its effective concentration against autophagy is hard to reach in an animal model, this invention shows vacuolin-1 and its analogues are better lead compounds for future clinical application against human cancer and malaria.

Materials and Methods

Antibodies and reagents—The antibodies used were as follows: LC3 (Novus; 1:1000 for the Western blotting analysis (WB)), p62 (Novus; 1:500 for the immunofluorescence analysis (IF) and 1:1000 WB), Cathepsin-L (BD Bioscience; 1:250 WB), EGFR (Santa Cruz; 1:250 WB), Rab5 (Cell Signaling; 1:1000 WB), GAPDH antibody (Sigma; 1:5000 WB). Vacuolin-1 was purchased from Santa Cruz. Bafilomycin A1, Chloroquine (CQ), and Glycyl-L-phenyl-alanine-β-naphthylamide (GPN) were purchased from Sigma-Aldrich. Fura-2 AM, lysosensor Green DND-189, and LysoSensorYellow/Blue DND-160 were purchased from Invitrogen.

Cell culture—HeLa, MCF-7, A549, and HepG2 cells (ATCC) were maintained in DMEM (Invitrogen) plus 10% fetal bovine serum (Invitrogen) and 100 units/ml of penicillin/streptomycin (Invitrogen) at 5% $CO_2$ and 37° C. PC3 cells were maintained in RPMI (Invitrogen) plus 10% fetal bovine serum (Invitrogen) and 100 units/ml of penicillin/streptomycin (Invitrogen) at 5% $CO_2$ and 37° C.

shRNA and lentivirus production and infection—Two optimal 21-mers were selected in the human Rab5A gene. One 21-mer was selected in the GFP gene as a control. These sequences were then cloned into the pLKO.1 vector for expressing shRNA. The production and infection were performed as described previously (Lu et al., 2013).

Intracellular $Ca^{2+}$ measurement—Cells were cultured in 24-well plates at the density of $7 \times 10^4$ cells/well in regular medium overnight and were labeled with 4 µM Fura-2 AM (Invitrogen) in regular HMSS at room temperature for 30 min. The cells were then washed with calcium-free HMSS containing 2 mM EGTA three times and incubated in the presence or absence of vacuolin-1 at room temperature for another 10 min. Cells were put on the stage of an Olympus inverted epifluorescence microscope and visualized using a 20× objective. Fluorescence images were obtained by alternate excitation at 340 nm and 380 nm with emission set at 510 nm. Images were collected by a CCD camera every 3 or 6 seconds and analyzed by Cell R imaging software.

Western blot and Immunofluorescence staining analyses—Both assays were performed as described previously (Lu et al., 2013).

Cell preparation for transmission electron microscopy (TEM)—Cell preparation for TEM was performed as described previously (Mi et al., 2007).

MTT cell proliferation assay—Cells were treated in four replicates and seeded into 96-well plate. Following drug treatment, MTT solution of 20 µl for every 100 µl medium was added to wells and incubated for 2 hours, followed by the addition of 150 µL of the DMSO solution to each well. The final reaction product, a purple formazan solution, was detected by a microplate reader (Techan infinite M200) for absorbance at a wavelength of 570 nm and a reference wavelength of 630 nm.

Lysosomal pH measurement—LysoSensor Green DND-189 is commonly used to measure the pH of acidic organelles, such as lysosomes, which become more fluorescent in acidic environments. Briefly, cells were loaded with 1 µMLysoSensor Green DND-189 in pre-warmed regular medium for 20 min at 37° C. Then the cells were washed twice with PBS and immediately analyzed by flow cytometry (collecting FL1 fluorescence and 10,000 cells were collected for each sample) or in a microplate reader (excitation/emission=485/530 nm).

Quantification of lysosomal pH was performed using a ratiometriclysosomal pH dye LysoSensor Yellow/Blue DND-160. The pH calibration curve was generated as described previously (Bankers-Fulbright et al., 2004). Briefly, cells were trypsinized and labeled with 2 µM Lysosensor Yellow/Blue DND-160 for 30 min at 37° C. in regular medium, and excessive dye was washed out using PBS. The labeled cells were treated for 10 min with 10 µM monensin and 10 µM nigericin in 25 mM 2-(N-morpholino) ethanesulfonic acid (MES) calibration buffer, pH 3.5-6.0, containing 5 mM NaCl, 115 mM KCl and 1.2 mM MgSO4. Quantitative comparisons were performed in a 96-well plate, and the fluorescence was measured with a microplate reader at 37° C. Light emitted at 440 and 535 nm in response to excitation at 340 and 380 nm were measured, respectively. The ratio of light emitted with 340 and 380 nm excitation was plotted against the pH values in IVIES buffer, and the pH calibration curve for the fluorescence probe was generated from the plot using Microsoft Excel.

V-ATPase assay—Fifth instar larvae of M. sexta (Lepidoptera, Sphingidae), weighing 6-8 g, were reared under long day conditions (16 h of light) at 27° C. using the gypsy moth diet (MP Biomedicals, Germany). The purification of the $V_1V_O$ holoenzyme was performed as previously described (Huss et al., 2002). Activity assays were performed in triplicate in a final volume of 160 µL and at a pH of 8.1. Assays contained 3 µg of purified $V_1V_0$ holoenzyme, 50 mM Tris-Mops, 3 mM 2-mercaptoethanol, 1 mM $MgCl_2$, 20 mM KCl, 0.003% $C_{12}E_{10}$, 20 mM NaCl, and 3 mM Tris-HCl. After 10 min of preincubation at 30° C., with or without inhibitors, 1 mM Tris-ATP was added and after an incubation for 2 min at 30° C. the reaction was stopped by freezing the samples in liquid nitrogen. Inorganic phosphate was determined as previously described (Wieczorek et al., 1990).

Glutathione S-Transferase (GST) Pull-Down Assay—Cells were collected and lysed in an ice-cold EBC lysis buffer described previously. Lysates were clarified by centrifugation at 13,000 g for 10 min at 4° C., and equal amount of protein (500 µg) from each supernatant was incubated with 30 µl of GST-RSBD bound to the 30 µl glutathione—Sepharose beads for 1 h at 4° C. on a rotating mixer. The beads was subsequently washed and resuspended in the standard SDS-sample buffer, boiled and subjected to SDS-PAGE (15% gel), followed by immunoblot analysis with the anti-Rab5 mAb.

Statistical analysis—Data were presented as mean±S.E.M. The statistical significance of differences was estimated by one-way ANOVA or Student's t-test. P<0.05 was considered significant.

EXAMPLES

Example 1

Figure 2:
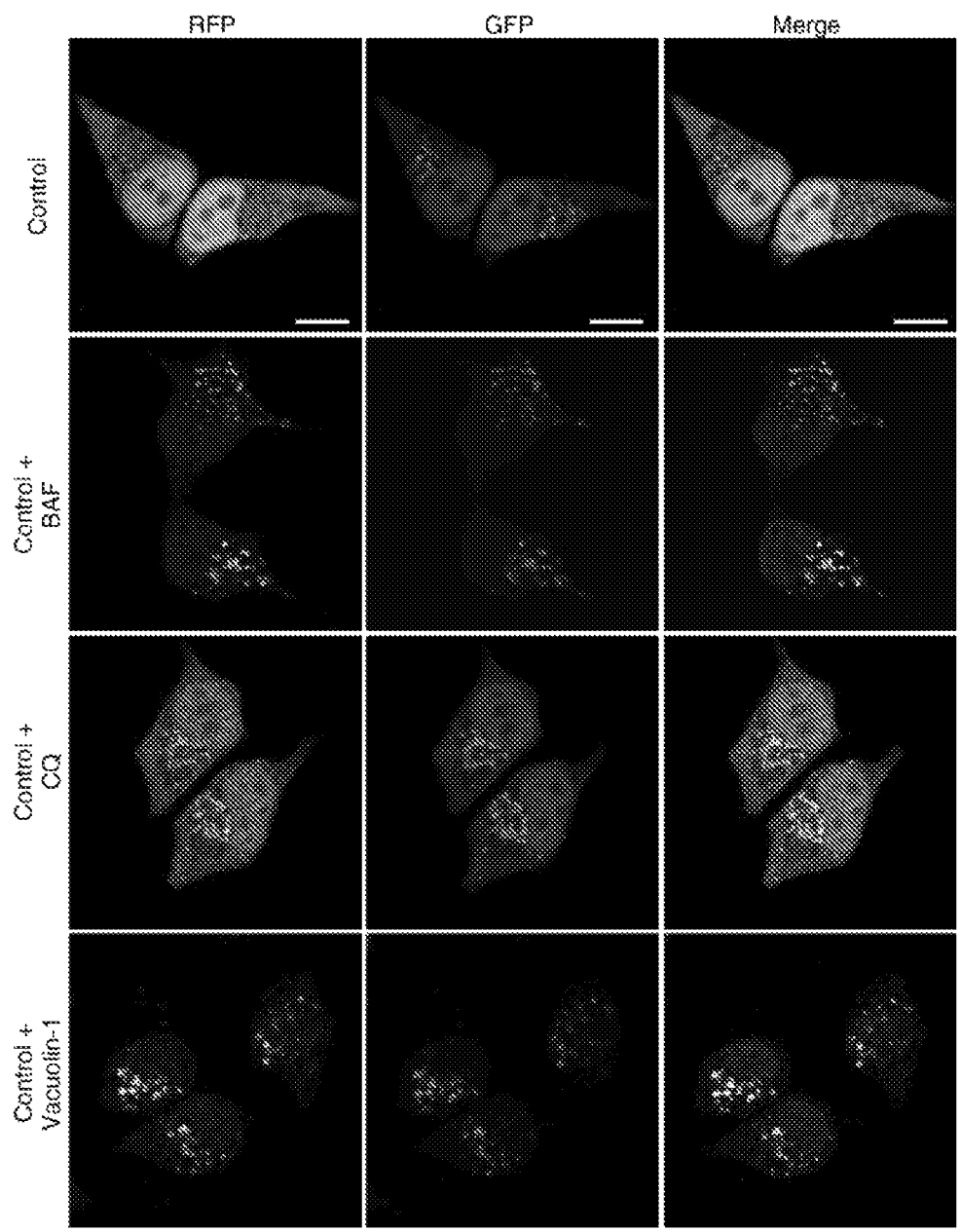
FIG. 2 shows immunofluorescence staining analysis of RFP-GFP-LC3 expressing HeLa cells following treatment with bafilomycin, CQ, and vacuolin-1.

The Small Chemical Vacuolin-1 Functions as an Autophagy Inhibitor by Inhibiting the Autophagosomal-Lysosomal Fusion in HeLa Cells Prompted by the fact that many available autophagy chemical modulators lack either potency or specificity (Kimura et al., 2013), a fluorescence image-based assay was set up to screen small molecules affecting autophagy. HeLa cells, an autophagy competent cell line, were infected with lentiviruses carrying expression cassettes that encode RFP-GFP-LC3 (tfLC3) (Kimura et al., 2007). Thus, the LC3-II positive autophagosomes are labeled with both GFP and RFP signals shown as yellow puncta, and after fusion with lysosomes, autolysosomes are shown as red only puncta because GFP loses its fluorescence in acidic pH. As shown in FIG. 2, starvation greatly induced the increase of both yellow and red only puncta, yet treatment of cells with bafilomycin (BAF), an inhibitor of the vacuolar proton pump that blocks the fusion of autophagosomes with lysosomes (Yamamoto et al., 1998), or CQ, markedly induced the accumulation of yellow puncta only, indicating that the autophagy is arrested at autophagasomes. These data indicate that RFP-GFP-LC3 expressing Hela cells can be used to monitor the progression of autophagy.

Figure 3A:
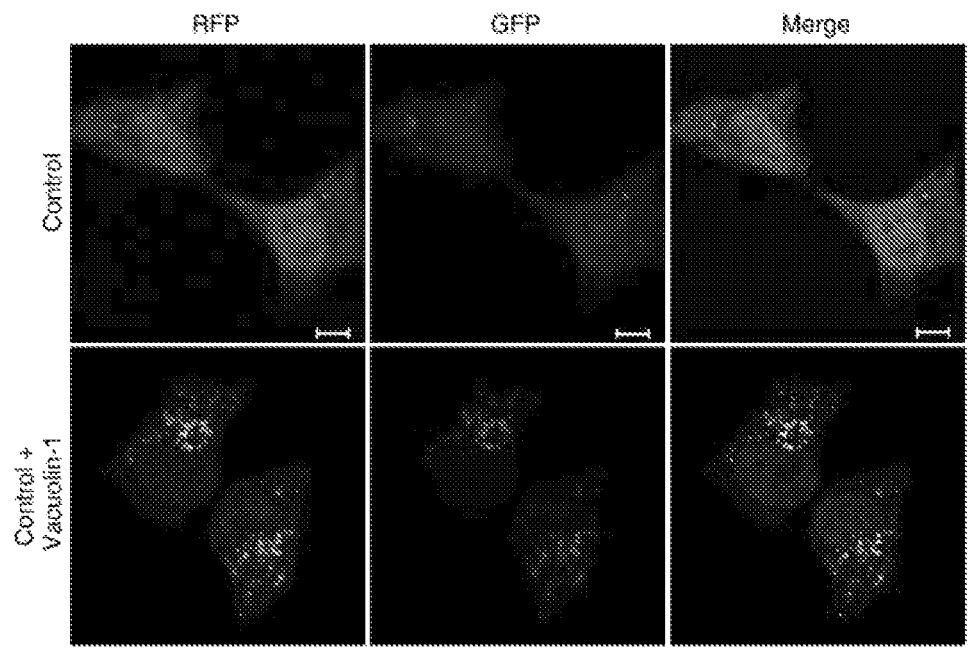
FIG. 3 shows vacuolin-1 inhibits the fusion between autophagosomes and lysosomes in HeLa cells. Immunofluorescence staining analysis of RFP-GFP-LC3 expressing HeLa cells following treatment with bafilomycin, CQ, and vacuolin-1 is shown. Scale bar=20 μM. (A) Percentage of yellow LC3II puncta in RFP-GFP-LC3 expressing HeLa cells following induction by vacuolin-1. (B) Western blot analysis showing induction of accumulation of both LC3-II and p62 in HeLa cells by vacuolin-1 (1 μM). (C) Immunofluorescence staining analysis of vacuolin-1 (1 μM) induction of GFP-LC3-II puncta in HeLa cells, which are not colocalized with RFP-Lamp1. Scale bar=20 μM. (D) Vacuolin-1 (1 μM) induces the accumulation of autophagic vacuoles as shown in the electron micrographs and highlighted in areas D1 and D2.
Figure 3A:
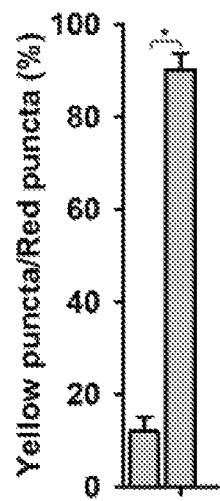
Figure 3B:
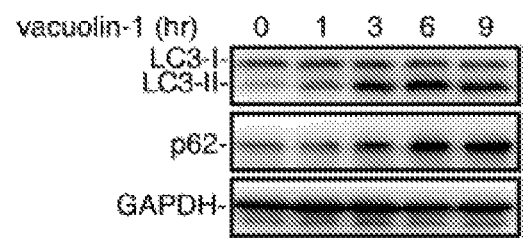
Figure 3C:
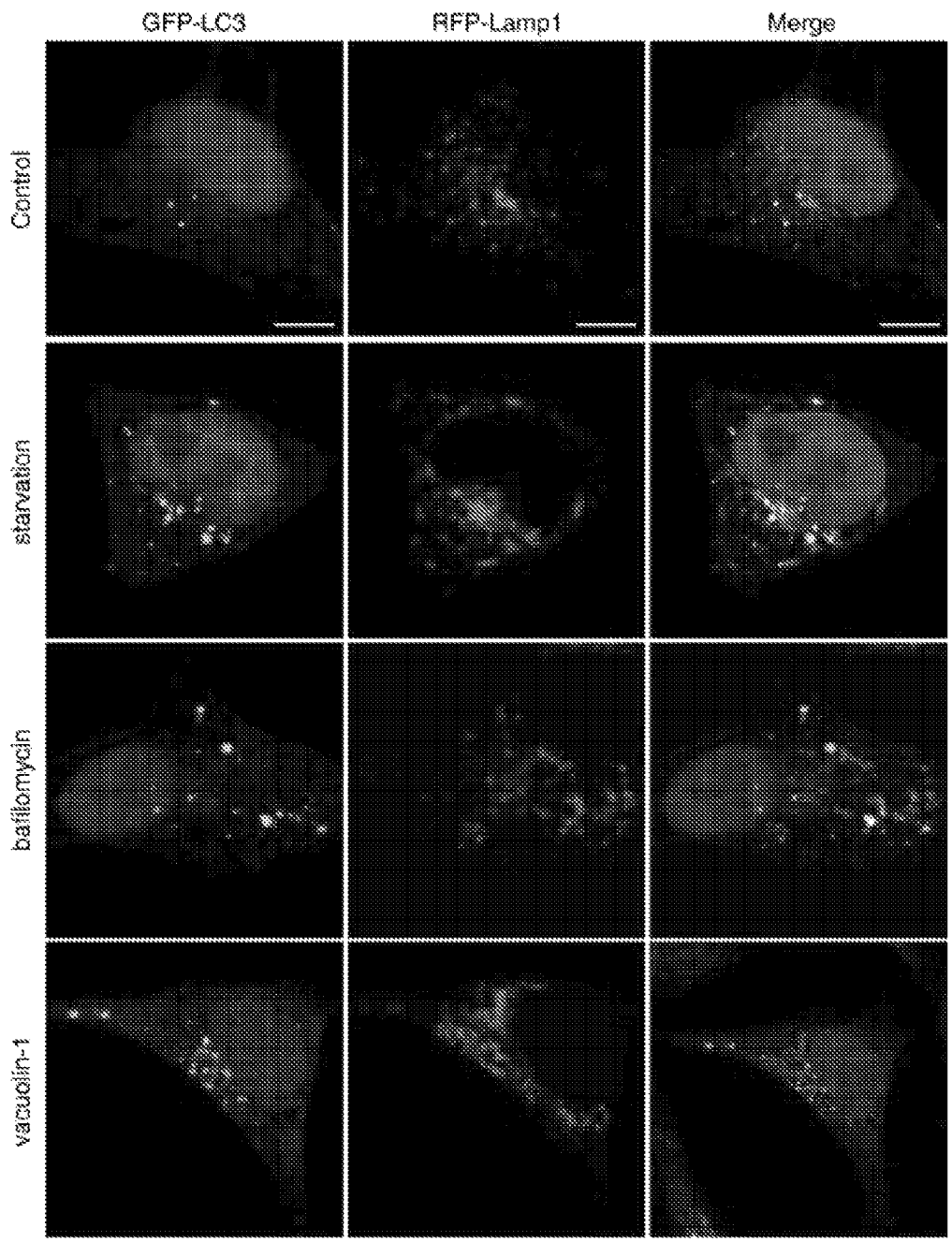
Figure 3D:
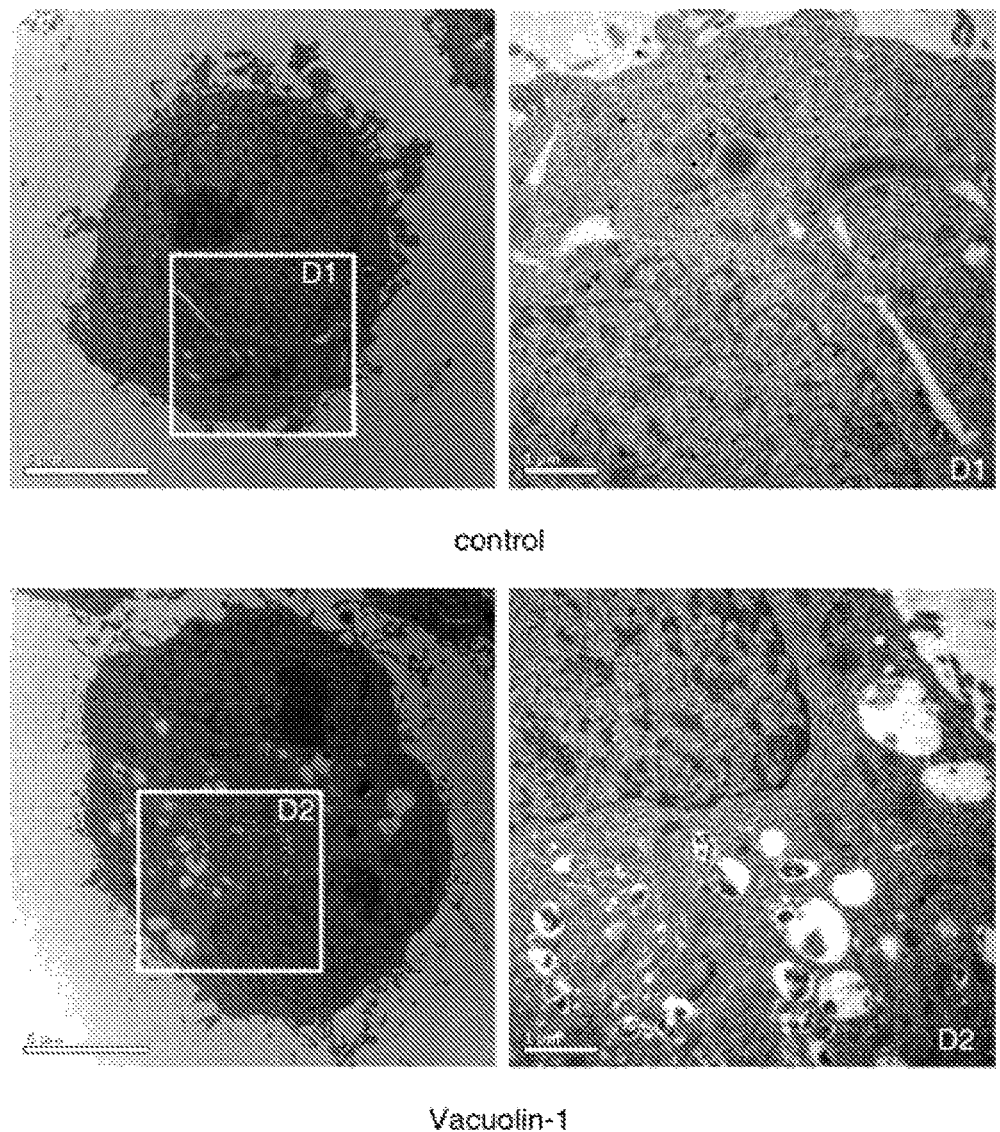

Next, a panel of small chemicals that are commercially available and have been previously shown to affect vesicle trafficking or organelle morphology were selected and screened for their effects on autophagy regulation in tfLC3 expressing HeLa cells (data not shown). One small chemical, vacuolin-1, potently induced LC3 yellow puncta, not red puncta (FIG. 3A). Similarly, western blot analyses confirmed that lipidated LC3-II was markedly increased in cells treated with vacuolin-1. p62, an autophagic substrate (Bjorkoy et al., 2006), was also accumulated in cells treated with vacuolin-1, suggesting that vacuolin-1 inhibits the fusion between autophagasome and lysosomes (FIG. 3B). Indeed, GFP-LC3 puncta were greatly increased in vacuolin-1 treated cells and did not co-localize with Lamp1, which was similar to the cells treated with BAF (FIG. 3C). Moreover, under the electron microscope, large numbers of autophagic vacuoles were observed in vacuolin-1 treated HeLa cells maintained in normal culture conditions (FIG. 3D). Taken together, these data indicate that vacuolin-1, similar to BAF or CQ, blocks the fusion between autophagosomes and autolysosomes, thereby leading to accumulation of LC3-II positive autophagosomes to achieve its effect of autophagy inhibition.

Example 2

Vacuolin-1 Potently and Reversibly Inhibits Autophagy but Shows Little Cell Toxicity Vacuolin-1 is a cell-permeable and water soluble triazine based compound. It has been previously reported that vacuolin-1 induced rapid homotypic fusion of endosomes and lysosomes to form large and swollen structures, yet it did not disturb cell cytoskeletal network (Cerny et al., 2004; Huynh and Andrews, 2005; Shaik et al., 2009). Amazingly, vacuolin-1 was at least ten times more potent than CQ in suppressing autophagy (FIGS. 4A and 5), yet it exhibited much less cell toxicity than CQ in a wide variety of cell types (FIGS. 4B and 6). Interestingly, the fusion block between autophagosomes and lysosomes was completely relieved 3 hours after removal of vacuolin-1 from the medium (FIG. 4C). Similarly, vacuolin-1 induced homotypic fusion between endosomes or lysosomes was recovered after removal of vacuolin-1 (data not shown). These data indicate that the effects of vacuolin-1 on autophagy inhibition or homortypic fusion are reversible.

Example 3

Vacuolin-1 Alkalinized Lysosomal pH and Decreased Lysosomal $Ca^{2+}$ Content

The mechanisms underlying vacuolin-1 induced autophagy arrest were explored. As lysosomal pH is essential for the fusion (Lu et al., 2013) and lysosomes were enlarged by vacuolin-1 treatment (Cerny et al., 2004; Huynh and Andrews, 2005; Shaik et al., 2009), it was examined whether vacuolin-1 affects lysosomal pH in these enlarged lysosomes. LysoSensor Green DND-189 ($pK_a$=~5.2) was first applied to qualitatively measure lysosomal pH (Davis-Kaplan et al., 2004). LysoSensor Green DND-189 permeates cell membranes and accumulates in acidic intracellular organelles, and its fluorescence increases or decreases in acidic or alkaline environments, respectively. As shown in FIG. 4D, vacuolin-1 treatment raised lysosomal pH in HeLa cells. Lysosomal pH was further quantified by a quantitative ratiometricLysoSensor Yellow/Blue DND-160 (DePedro and Urayama, 2009) stained cells and found that lysosomal pH in vacuolin-1 treated HeLa cells was increased from pH 4.7 in control cells to pH 5.2 (FIG. 4E). Thus, it is clear that vacuolin-1 alkalinizes lysosomalpH.

Since lysosome is also a major intracellular $Ca^{2+}$ pool, and $Ca^{2+}$ and protons are tightly coupled in lysosomes (Morgan et al., 2011), it was also assessed whether vacuolin-1 treatment affects the lysosomal $Ca^{2+}$ content. Treatment of cells with glycyl-1-phenylalanine 2-naphthylamide (GPN) selectively disrupts the lysosomal membrane (Jadot et al., 2001), thereby releasing the lysosomal $Ca^{2+}$ (Srinivas et al., 2002). As shown in FIG. 4F, pretreatment of cells with vacuolin-1 significantly lowered the ability of GPN induced lysosomal $Ca^{2+}$ release, suggesting that vacuolin-1 decreases lysosomal $Ca^{2+}$ levels as well.

Example 4

Vacuolin-1 Inhibited General Endosomal-Lysosomal Degradation in HeLa Cells

Figure 7A:
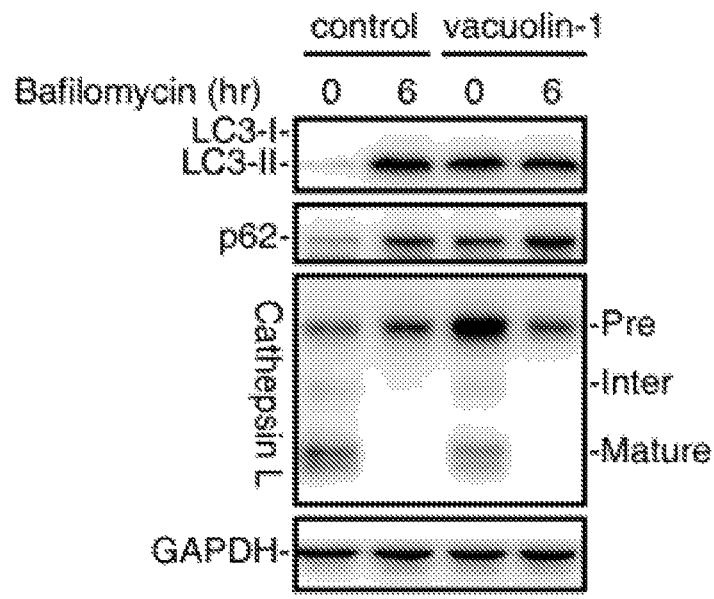
FIG. 7 shows (A) western blot analyses against LC3, p62, and cathepsin L in HeLa cells treated with or without vacuolin-1 (1 μM) or bafilomycin (100 nM); (B) western blot analyses against EGFR in HeLa cells following an EGFR degradation assay (treatment of HeLA cells with EGF in the presence or absence of vacuolin-1); (C) immunofluorescence staining analysis for EGFR in HeLa cells treated with vacuolin-1 (1 μM) (Scale bar=20 μM); and (D) flow cytometric analysis for DQ-BSA-green fluorescence in vacuolin-1 (1 μM) treated and control HeLa cells.
Figure 7B:
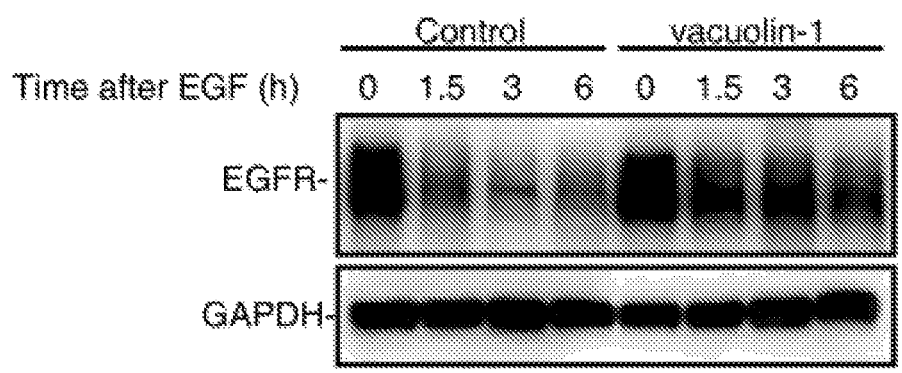
Figure 7C:
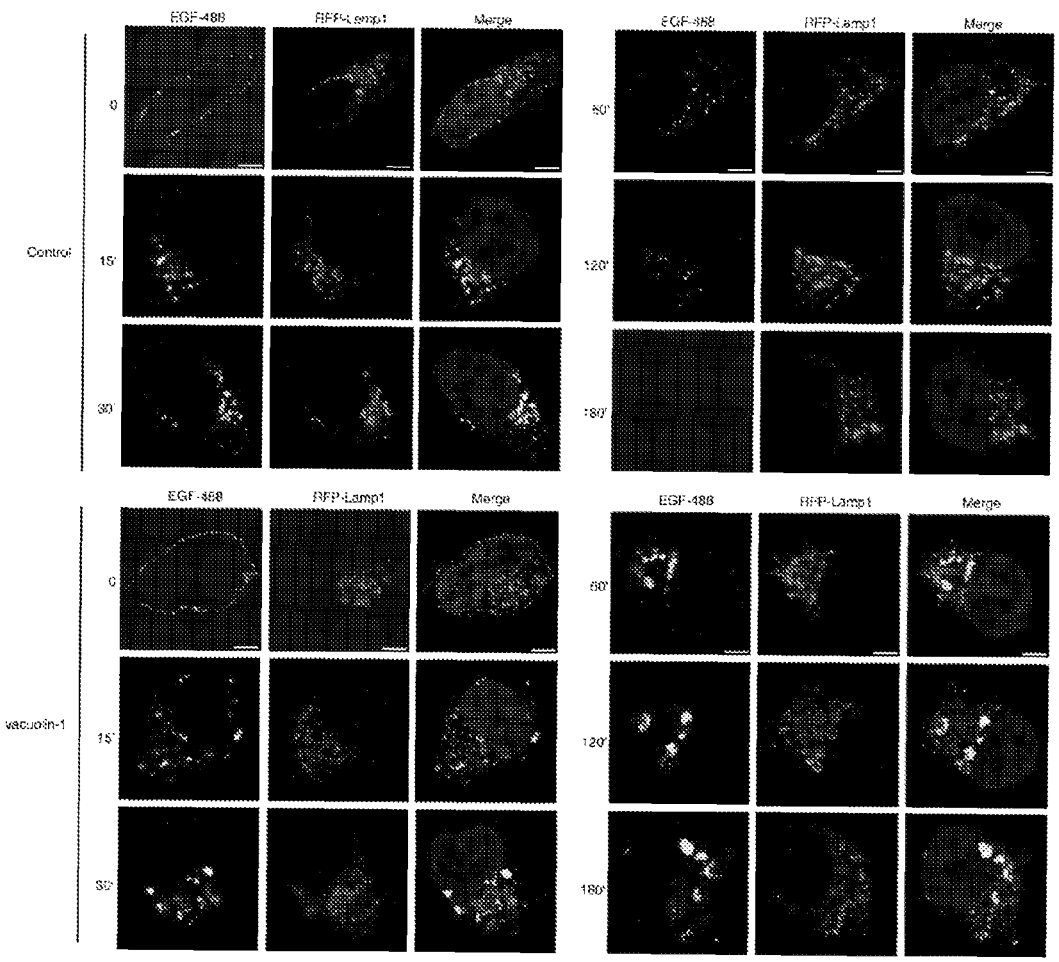
Figure 7D:
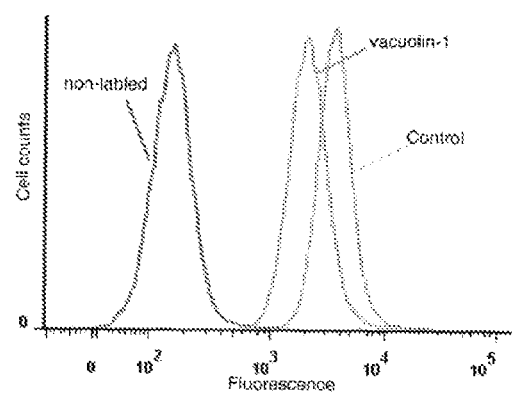

Since the increase of lysosomal pH normally compromises the lysosomal activity, it was assessed whether vacuolin-1 affects the general lysosomal functions to inhibit autophagy maturation. The processing of cathepsin L from the precursor form to its mature form has been commonly used as a marker for lysosomal activity, and it was found that the processing of cathepsin L into its mature form was not affected in vacuolin-1 treated HeLa cells, but vacuolin-1 did markedly increase the levels of immature form of cathepsin L (FIG. 7A). Next, an epidermal growth factor receptor (EGFR) degradation assay was performed to examine whether vacuolin-1 affects the general endosomal-lysosomal pathway. In this assay, HeLa cells were treated with EGF in the presence or absence of vacuolin-1. After EGF binds to its receptors (EGFR), the receptor complex undergoes endocytosis and is targeted tolysosomes for degradation. As shown in FIG. 7B, vacuolin-1 inhibited EGF-triggered EGFR degradation. Interestingly, EGFR was internalized normally but the endosomes containing EGFR failed to fuse with lysosomes; this explains the accumulation of EGFR in vacuolin-1 treated cells (FIG. 7C). Similarly, a DQ-BSA-green degradation assay was applied to measure the general endosomal-lysosomal degradation. DQ-BSA-green is a BSA labeled with a self-quenching fluorescent dye. After DQ-BSA-green is delivered to lysosomes via endocytosis, it is hydrolyzed into single dye-labeled peptides by lysosomal proteases, thereby relieving self-quenching and the fluorescence can subsequently be monitored by flow cytometry. As shown in FIG. 7D, vacuolin-1 markedly inhibited the degradation of BSA by lysosomes, yet DQ-BSA-Green was present in endosomes but failed to be delivered to lysosomes (data not shown). Collectively, these results support that vacuolin-1 inhibits the general endosomal-lysosomal degradation, which might be due to the alkalized lysosomal pH arresting the fusion of endosomes with lysosomes.

Example 5

Rab5 was Required for Vacuolin-1 Induced Autophagy Arrest and Endosomal Fusion

Figure 8A:
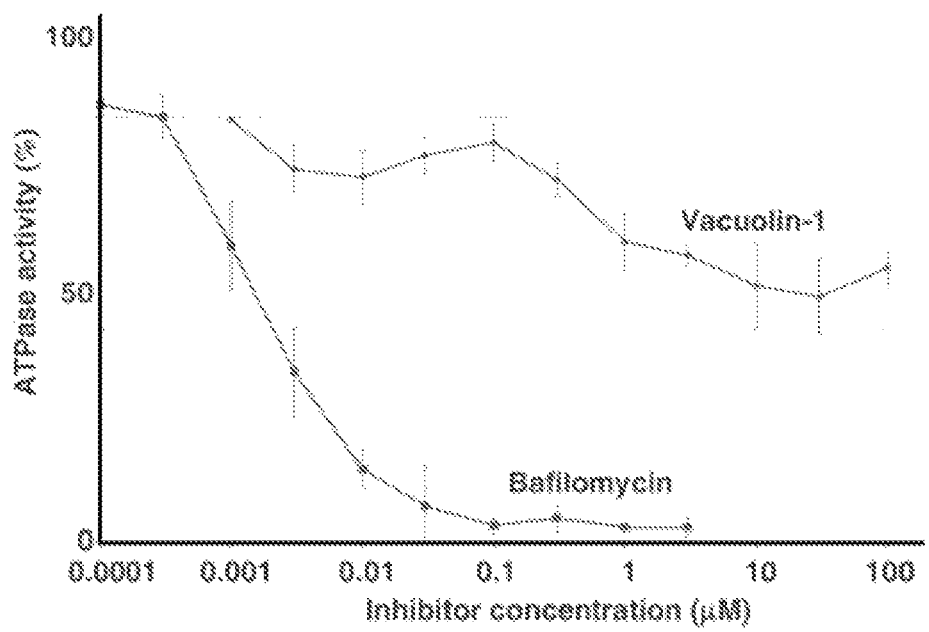
FIG. 8 shows (A) an in vitro V-ATPase assay showing V-ATPase activity in vacuolin-1 and bafilomycin treated cells; (B) results of a GST-tagged Rabaptin5 pull-down assay in HeLa cells showing active Rab5 in cells treated with vacuolin-1 (1 μM) or transfected with Rab5A-CA or Rab5A-DN; (C) western blot analysis against LC3-II and p62 in HeLa cells showing Rab5A knockdown blocks vacuolin-1 induced accumulation of LC3-II and p62; (D) expression of Rab5A-CA enhances vacuolin-1 induced autophagy arrest, whereas expression of Rab5A-DN blocks it in HeLa cells; (E) western blot analysis against LC3-II and p62 following expression of Rab5A-CA; and (F) immunostaining analysis against LC3-II and p62 following expression of Rab5A-CA (scale bar=20 μM).
Figure 8B:
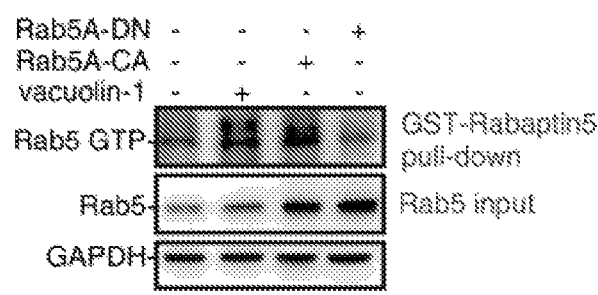
Figure 8C:
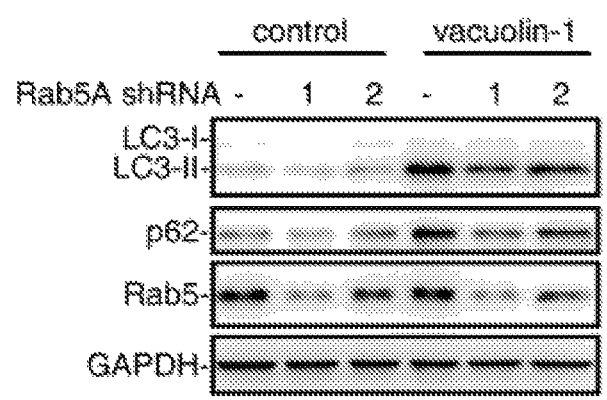
Figure 8D:
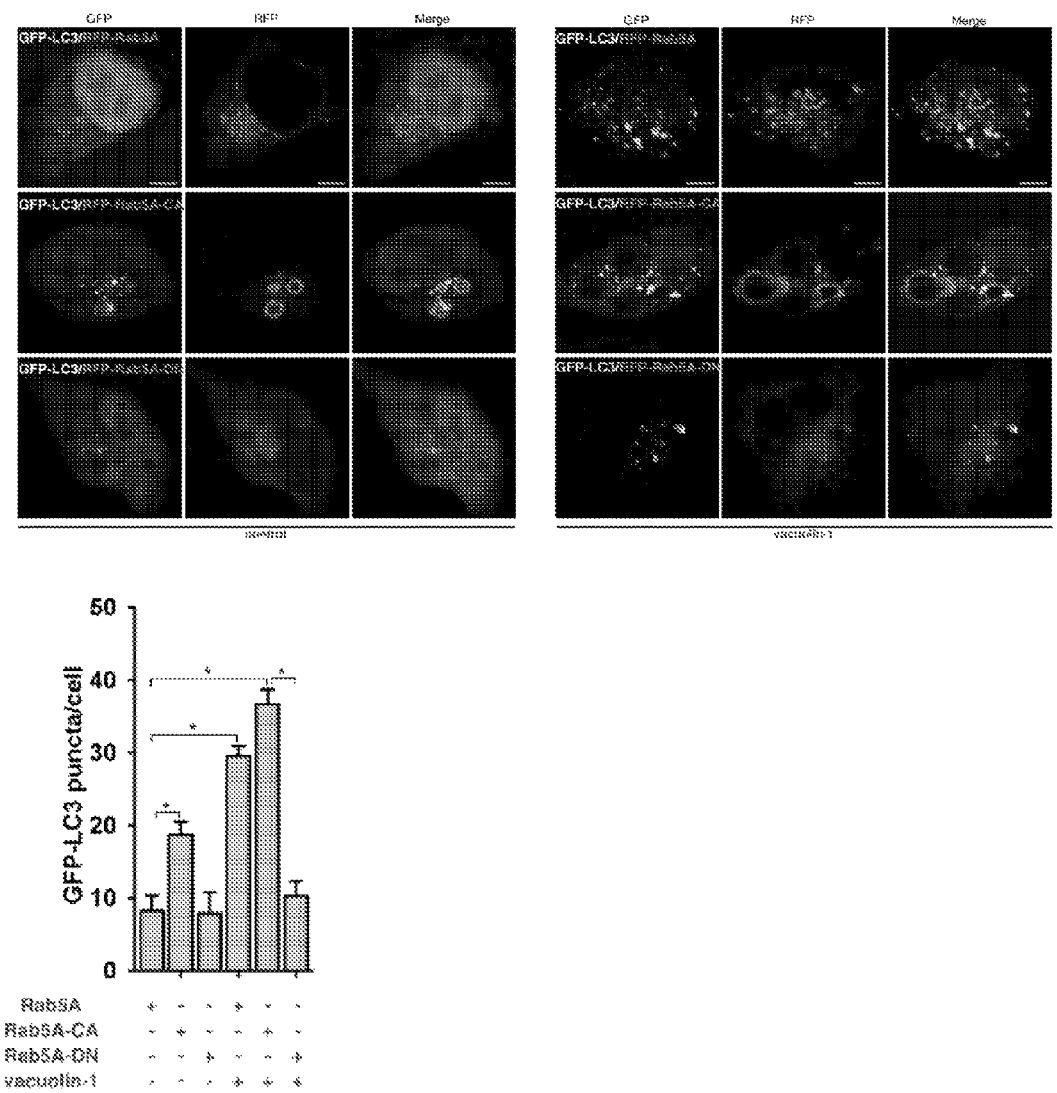
Figure 8E:
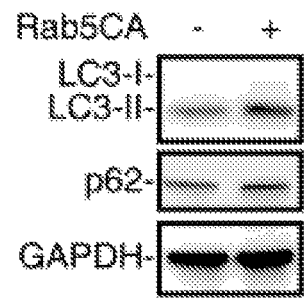
Figure 8F:
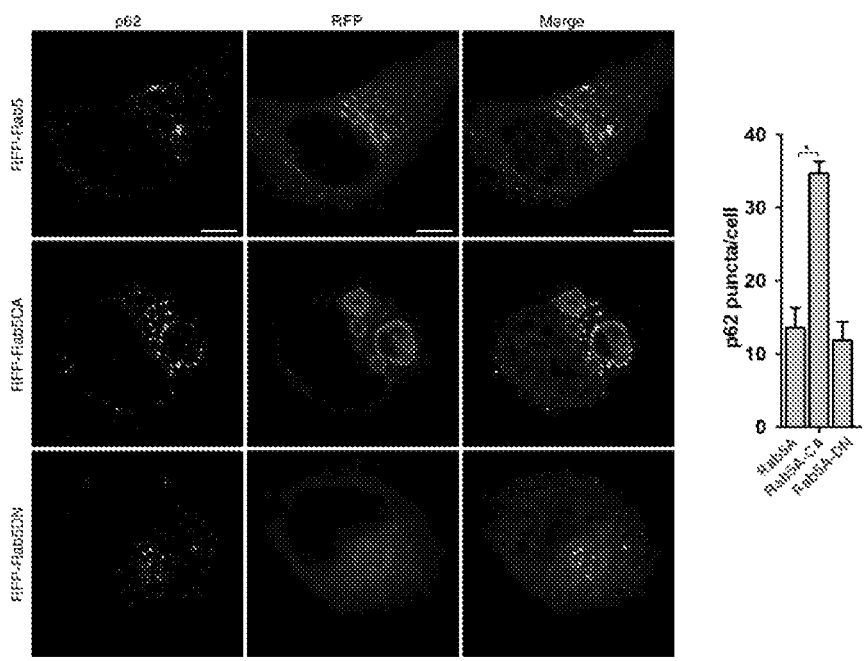
Figure 9:
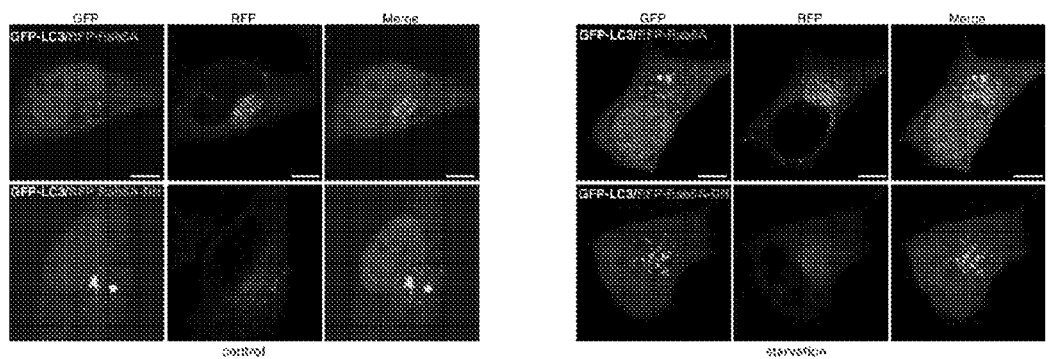
FIG. 9 shows expression of Rab5A-DN does not affect starvation induced LC3 puncta in HeLa cells.
Figure 10:
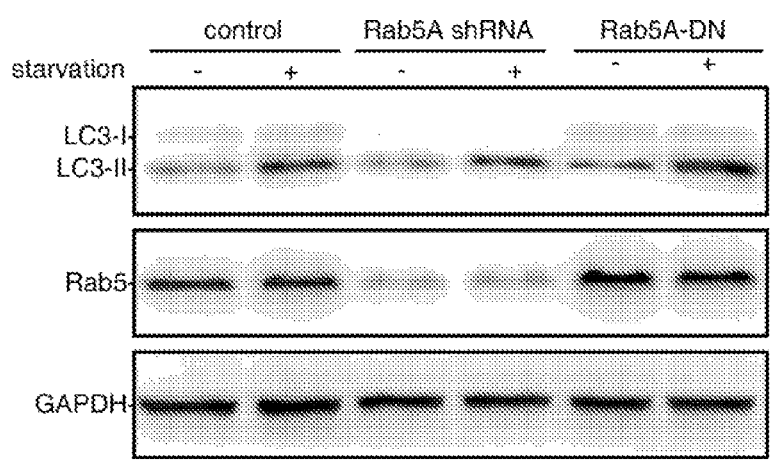
FIG. 10 shows Rab5A knockdown or expression of Rab5A-DN does not affect starvation induced LC3-II in HeLa cells.
Figure 11A:
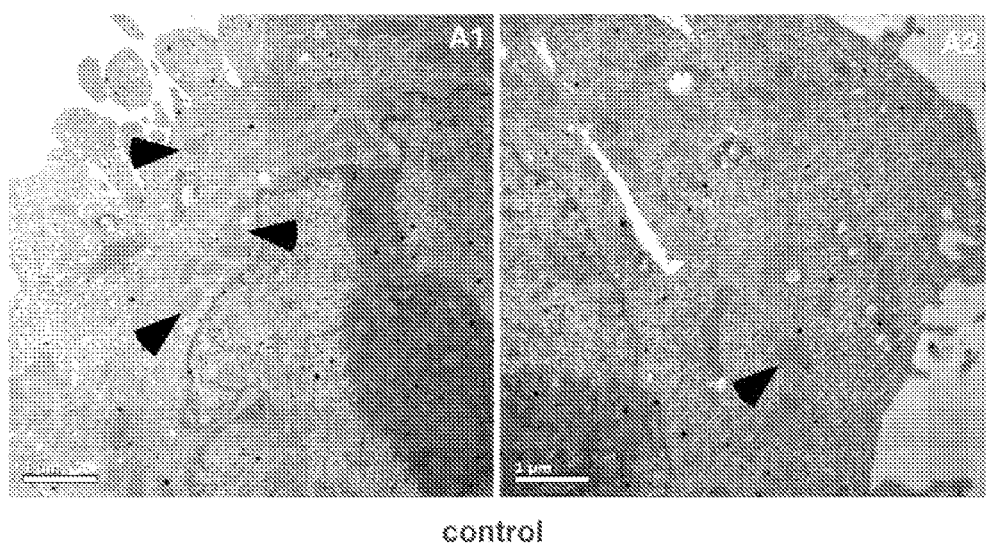
FIG. 11 shows an electron micrograph of enlarged lysosomes in HeLa cells following vacuolin-1 treatment (B) versus control (A).
Figure 11B:
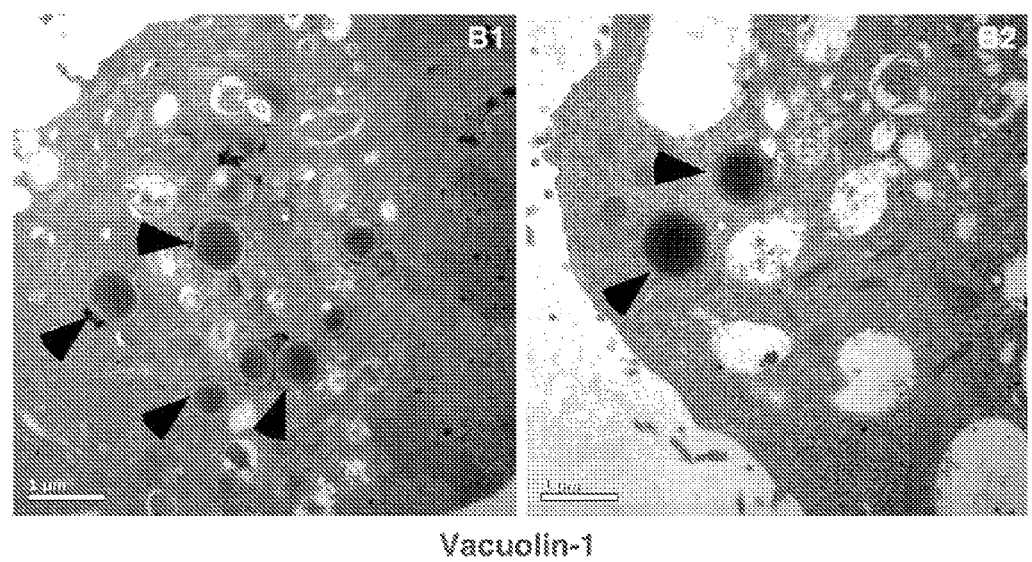
Figure 12:
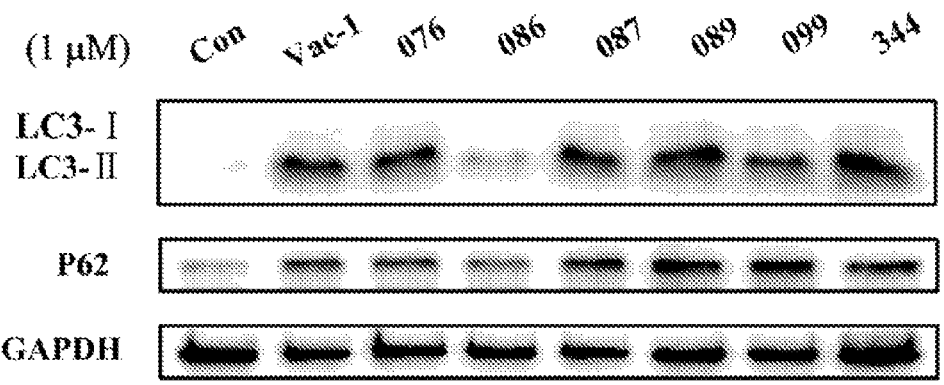
FIG. 12 shows vacuolin-1 analogues inhibit the fusion between autophagosomes and lysosomes in HeLa cells. Western blot analysis against LC3-I, LC3-II, and p62.

Although vacuolin-1 increased lysosomal pH, vacuolin-1 had little effects on V-ATPase activity in vitro (FIG. 8A). Vacuolin-1 also induced the homotypic fusion of endosomes or lysosomes, and Rab5, a small GTPase, is essential for endosome fusion (Zeigerer et al., 2012). Therefore, it was examined whether vacuolin-1 activates Rab5 to indirectly change lysosomal pH. Indeed, vacuolin-1 markedly activated Rab5, as shown by a GST-tagged Rabaptin5 pull-down assay, which specifically interacts with Rab5-GTP, not Rab5-GDP (FIG. 8B) (Liu et al., 2007). Consistently, Rab5A knockdown markedly decreased vacuolin-1 induced accumulation of both LC3-II and p62 (FIG. 8C). Similarly, overexpression of a dominant-negative form of Rab5A (Rab5A-DN) blocked vacuolin-1 induced autophagy arrest and homotypic fusion, whereas overexpression of a constitutive form of Rab5A (Rab5A-CA) (Bohdanowicz et al., 2012) augmented the ability of vacuolin-1 induced autophagy arrest and homotypic fusion (FIG. 8D). Interestingly, Rab5A-CA overexpression alone also blocked the autophagosomal-lysosomal fusion, thereby inducing the accumulation of LC3-II and p62 (FIGS. 8E and 8F). Notably, Rab5A-DN expression or Rab5A knockdown did not affect starvation-induced autophagy (FIGS. 9 and 10). Taken together, these data indicate that Rab5A is required for vacuolin-1 induced autophagy arrest.

Example 6

Figure 16:
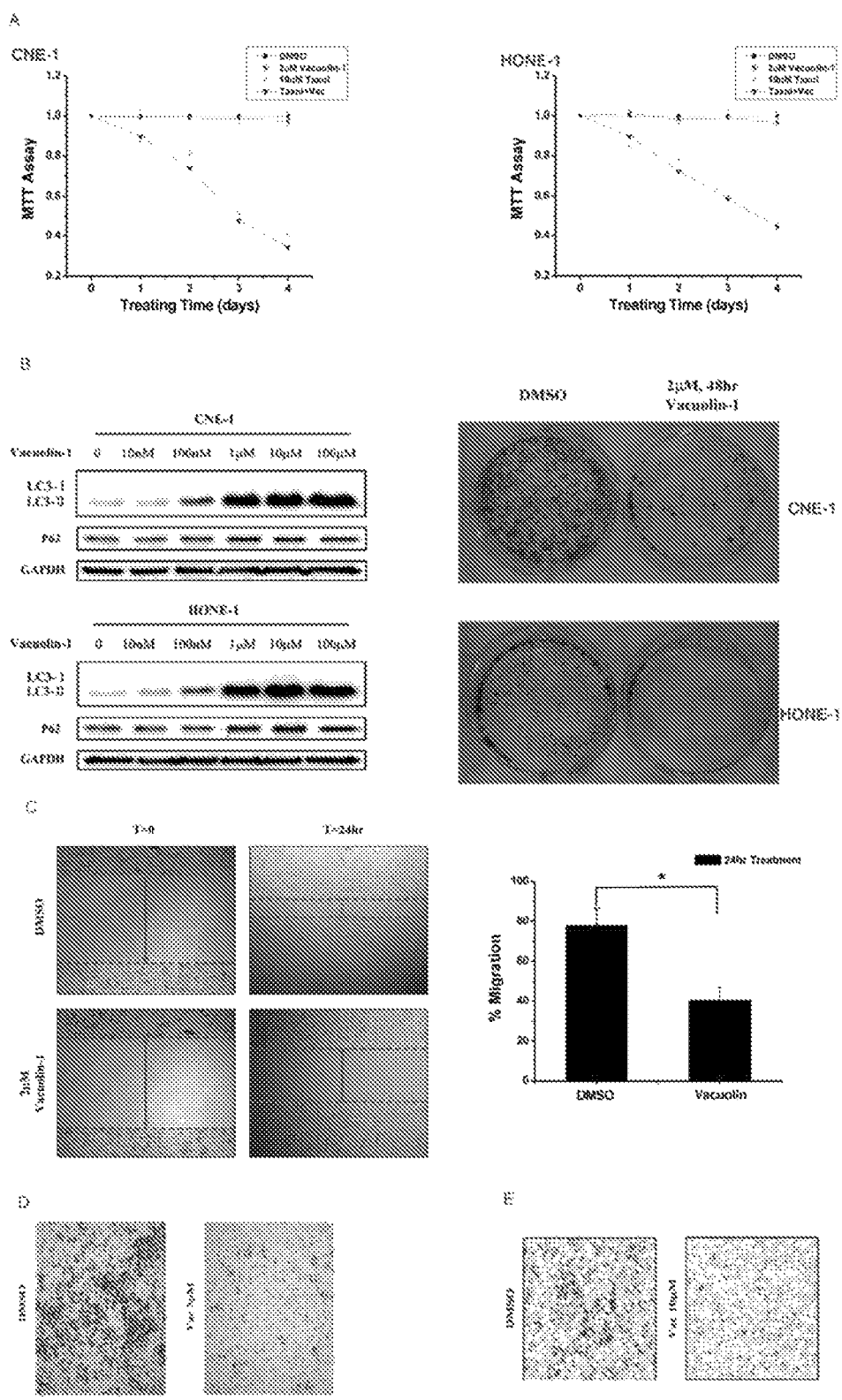
FIG. 16 shows vacuolin-1 markedly inhibited colony formation and migration of human nasopharyngeal carcinomas. (A) Vacuolin-1 treatment alone displayed little cell toxicity in CNE-1 or HONE-1 cells. (B) Vacuolin-1 dramatically reduced the size and number of colonies generated from single CNE-1 or HONE-1 cell. (C) Vacuolin-1 efficiently suppressed the migration of both CNE-1 and HONE-1 cells as revealed by the observation that vacuolin-1 treatment induced a marked decrease in motility of tumor cell. (D) and (E) Vacuolin-1 markedly inhibited the migration (D) and invasiveness (E) of CNE-1 and HONE-1 cells.

Vacuolin-1 Markedly Inhibited Colony Formation and Migration of Human Nasopharyngeal Carcinomas Although CQ has already been applied to treat a wide spectrum of human cancers, CQ induces ocular or renal toxicity and easily triggers drug resistance (Kimura et al., 2013). We, thus, assessed whether vacuolin-1 exhibits any anti-tumor ability and whether it can, like CQ, potentiate the sensitivity of tumor cells to chemotherapeutic drugs. We first investigated the anti-tumor effects of vacuolin-1 in two nasopharyngeal carcinoma cell lines, CNE-1 and HONE-1. As shown in FIG. 16A, vacuolin-1 treatment alone displayed little cell toxicity in CNE-1 or HONE-1 cells. Surprisingly, vacuolin-1 also showed almost no synergistic effects on inhibiting tumor cell proliferation in combination with several clinical anti-tumor drugs, such as taxol, 5-FU, and temsirolimus (FIG. 16A and data not shown). Alternatively, colony formation assay was performed to assess whether vacuolin-1 affects the ability of a single tumor cell to grow into a colony. As shown in FIG. 16B, vacuolin-1 dramatically reduced the size and number of colonies generated from single CNE-1 or HONE-1 cell. We subsequently performed wound healing assay to assess whether vacuolin-1 affects the migration of tumor cells. Strikingly, vacuolin-1 efficiently suppressed the migration of both CNE-1 and HONE-1 cells as revealed by the observation that vacuolin-1 treatment induced a marked decrease in motility of tumor cell (FIG. 16C and data not shown). Likewise, vacuolin-1 markedly inhibited the migration and invasiveness of CNE-1 and HONE-1 cells (FIG. 16D, FIG. 16E, and data not shown). Obviously, vacuolin-1 is an efficient anti-tumor agent in vitro.

Example 7

Figure 17:
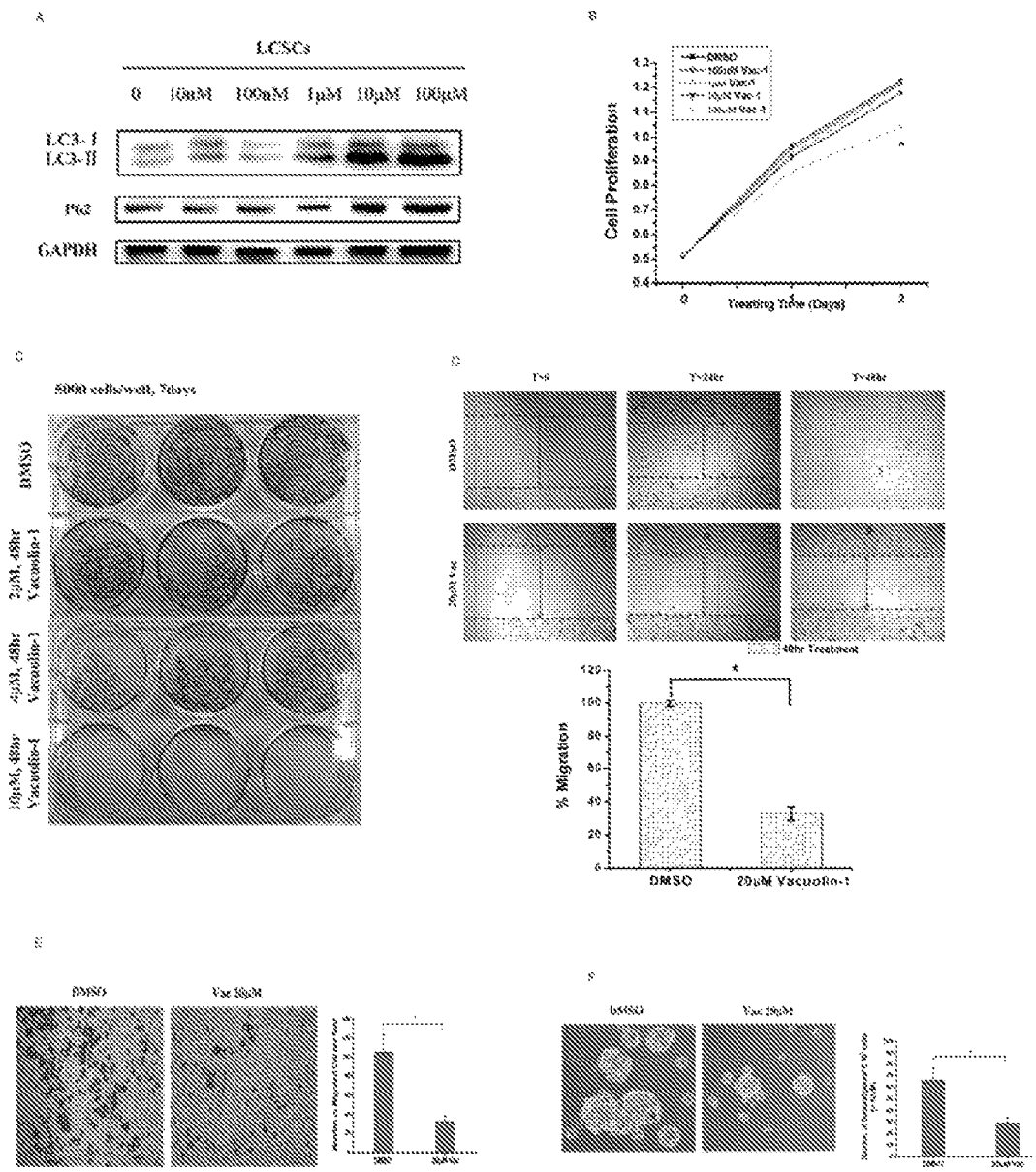
FIG. 17 shows vacuolin-1 markedly inhibited colony formation and migration of human lung cancer stem cells (LCSCs) in vitro. (A) Vacuolin-1 on autophagy inhibition in human lung cancer stem cells (hLCSCs) were 10 times less potent than those in other tumor cell lines. (B) Vacuolin-1 did not affect the cell proliferation of hLCSCs. (C-F)) Vacuolin-1 (>10 μM) almost completely inhibited the colony formation (C), migration (D), invasion (E) and tumor sphere formation (F) of hLCSCs.

Vacuolin-1 Markedly Inhibited Colony Formation and Migration of Human Lung Cancer Stem Cells (LCSCs) In Vitro Cancer stem cells (CSCs), a subpopulation of cells within tumors, actually drive tumor growth and recurrence. CSCs are resistant to many current cancer treatments, including chemo- and radiation therapy, thus they can survive these therapy to regenerate new tumors. CSCs have been shown to possess stem cell characteristics, such as self-renewal, stress and drug resistance, and enhanced migration, all of which have been implicated in disease recurrence and distant metastasis (Gupta et al., 2009). Therefore, it is of great interest to assess the anti-tumor effects of vacuolin-1 on CSCs. Indeed, vacuolin-1 on autophagy inhibition in human lung cancer stem cells (hLCSCs) were 10 times less potent than those in other tumor cell lines (FIG. 17A), and vacuolin-1 did not affect the cell proliferation of hLCSCs (FIG. 17B). Likewise, vacuolin-1 (>10 μM) almost completely inhibited the colony formation, migration, invasion and tumor sphere formation of hLCSCs (FIG. 17C-17F). Collectively, these data indicate that vacuolin-1 can efficiently suppress the tumorigenic potential of lung cancer stem cells in vitro.

Example 8

Vacuolin-1 Markedly Suppressed Tumor Growth in Nude Mice

Figure 18:
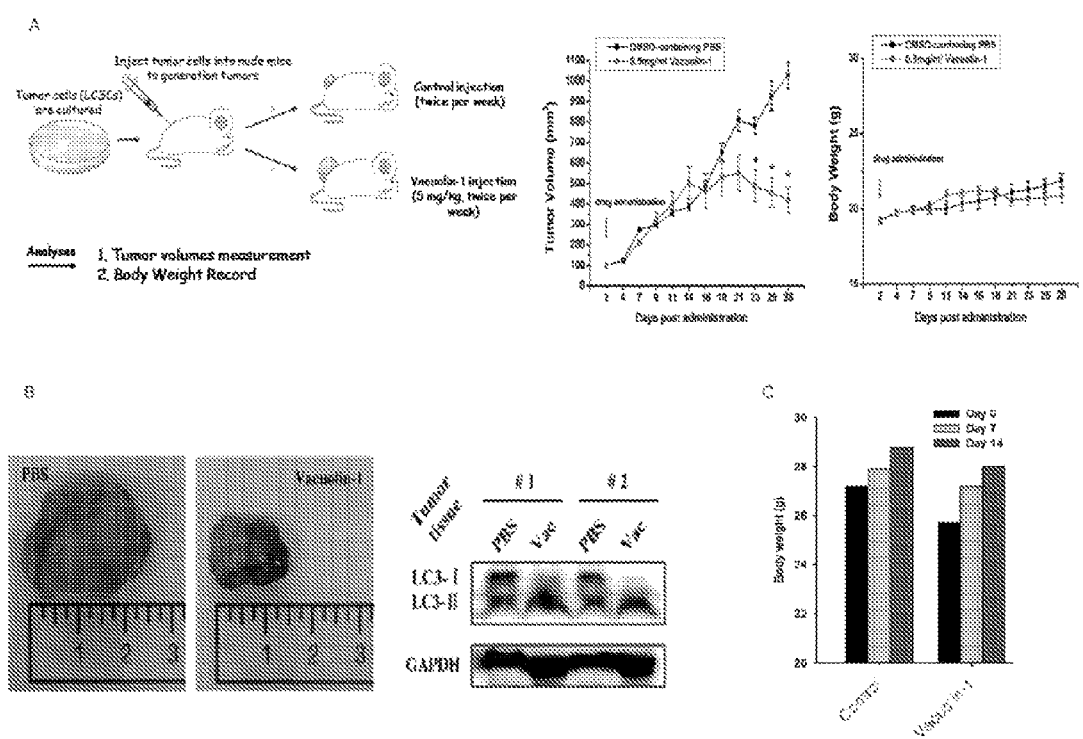
FIG. 18 shows vacuolin-1 markedly suppressed tumor growth in nude mice. (A). Intratumoral injection of vacuolin-1 (5 mg/kg) twice a week markedly inhibited tumor growth of LCSC xenograft in nude mice but had little effects on the weight gain. (B) vacuolin-1 treatment markedly inhibited autophagy in tumors. (C) Intraperitoneal injection of vacuolin-1 (250 mg/kg) in young adult mice exhibited little acute toxicity as the drug injected mice showed normal activity and weight gain as compared to control after two weeks.

Promoted by the fact that vacuolin-1 potently inhibited the migration and colony formation ability of human nasopharyngeal carcinomas cells and human lung cancer stem cells in vitro, we examined the ability of vacuolin-1 to inhibit tumor progression in xenograft mouse model. We first assessed the ability of vacuolin-1 to suppress LCSC tumor xenograft in BALB/c nude mice. Briefly, $1\times10^4$ lung cancer stem cells (LCSCs, $3^{rd}$ generation) were suspended in Matrigel (BD Biosciences) at a ratio of 1:1, and 200 iL of cells was subcutaneously injected into the back of nude mice. The tumor volume was measured every five days after injection and calculated from the formula: length×width×depth×$\pi$/6. Mice were removed from the study when their tumor volumes exceed 2000 mm$^3$ (FIG. 18A). As shown in FIG. 18A, intra tumoral injection of vacuolin-1 (5 mg/kg) twice a week markedly inhibited tumor growth of LCSC xenograft in nude mice but had little effects on the weight gain. As expected, vacuolin-1 treatment markedly inhibited autophagy in tumors (FIG. 18B). Also, we tested the acute toxicity of vacuolin-1 in mice. Intraperitoneal injection of vacuolin-1 (250 mg/kg) in young adult mice exhibited little acute toxicity as the drug injected mice showed normal activity and weight gain as compared to control after two weeks (FIG. 18C). Taken together, these data indicate that vacuolin-1 is a promising anti-tumor agent in vivo with tolerable toxicity.

REFERENCES

Amaravadi, R. K., Yu, D., Lum, J. J., Bui, T., Christophorou, M. A., Evan, G. I., Thomas-Tikhonenko, A., and Thompson, C. B. (2007). Autophagy inhibition enhances therapy-induced apoptosis in a Myc-induced model of lymphoma. The Journal of clinical investigation 117, 326-336.

Baek, K. H., Park, J., and Shin, I. (2012). Autophagy-regulating small molecules and their therapeutic applications. Chemical Society reviews 41, 3245-3263.

Bankers-Fulbright, J. L., Kephart, G. M., Bartemes, K. R., Kita, H., and O'Grady, S. M. (2004). Platelet-activating factor stimulates cytoplasmic alkalinization and granule acidification in human eosinophils. Journal of cell science 117, 5749-5757.

Bjorkoy, G., Lamark, T., and Johansen, T. (2006). p62/SQSTM1: a missing link between protein aggregates and the autophagy machinery. Autophagy 2, 138-139.

Bohdanowicz, M., Balkin, D. M., De Camilli, P., and Grinstein, S. (2012). Recruitment of OCRL and Inpp5B to phagosomes by Rab5 and APPL1 depletes phosphoinositides and attenuates Akt signaling. Molecular biology of the cell 23, 176-187.

Cerny, J., Feng, Y., Yu, A., Miyake, K., Borgonovo, B., Klumperman, J., Meldolesi, J., McNeil, P. L., and Kirchhausen, T. (2004). The small chemical vacuolin-1 inhibits Ca(2+)-dependent lysosomal exocytosis but not cell resealing. EMBO reports 5, 883-888.

Davis-Kaplan, S. R., Ward, D. M., Shiflett, S. L., and Kaplan, J. (2004). Genome-wide analysis of iron-dependent growth reveals a novel yeast gene required for vacuolar acidification. The Journal of biological chemistry 279, 4322-4329.

DePedro, H. M., and Urayama, P. (2009). Using LysoSensor Yellow/Blue DND-160 to sense acidic pH under high hydrostatic pressures. Analytical biochemistry 384, 359-361.

Gupta, P. B., Onder, T. T., Jiang, G., Tao, K., Kuperwasser, C., Weinberg, R. A., and Lander, E. S. (2009). Identification of selective inhibitors of cancer stem cells by high-throughput screening. Cell 138, 645-659.

Hanson, K. K., Ressurreicao, A. S., Buchholz, K., Prudencio, M., Herman-Ornelas, J. D., Rebelo, M., Beatty, W. L., Wirth, D. F., Hanscheid, T., Moreira, R., et al. (2013). Torins are potent antimalarials that block replenishment of *Plasmodium* liver stage parasitophorous vacuole membrane proteins. Proceedings of the National Academy of Sciences of the United States of America 110, E2838-2847.

Hidvegi, T., Ewing, M., Hale, P., Dippold, C., Beckett, C., Kemp, C., Maurice, N., Mukherjee, A., Goldbach, C., Watkins, S., et al. (2010). An autophagy-enhancing drug promotes degradation of mutant alpha1-antitrypsin Z and reduces hepatic fibrosis. Science 329, 229-232.

Huotari, J., and Helenius, A. (2011). Endosome maturation. The EMBO journal 30, 3481-3500.

Huss, M., Ingenhorst, G., Konig, S., Gassel, M., Drose, S., Zeeck, A., Altendorf, K., and Wieczorek, H. (2002). Concanamycin A, the specific inhibitor of V-ATPases, binds to the $V_O$ subunit c. J Biol Chem 277, 40544-40548.

Huynh, C., and Andrews, N. W. (2005). The small chemical vacuolin-1 alters the morphology of lysosomes without inhibiting Ca2+-regulated exocytosis. EMBO reports 6, 843-847.

Jadot, M., Andrianaivo, F., Dubois, F., and Wattiaux, R. (2001). Effects of methylcyclodextrin on lysosomes. Eur J Biochem 268, 1392-1399.

Janku, F., McConkey, D. J., Hong, D. S., and Kurzrock, R. (2011). Autophagy as a target for anticancer therapy. Nature reviews Clinical oncology 8, 528-539.

Kimura, S., Noda, T., and Yoshimori, T. (2007). Dissection of the autophagosome maturation process by a novel reporter protein, tandem fluorescent-tagged LC3. Autophagy 3, 452-460.

Kimura, T., Takabatake, Y., Takahashi, A., and Isaka, Y. (2013). Chloroquine in cancer therapy: a double-edged sword of autophagy. Cancer research 73, 3-7.

Liu, J., Lamb, D., Chou, M. M., Liu, Y. J., and Li, G. (2007). Nerve growth factor-mediated neurite outgrowth via regulation of Rab5. Molecular biology of the cell 18, 1375-1384.

Lock, R., Roy, S., Kenific, C. M., Su, J. S., Salas, E., Ronen, S. M., and Debnath, J. (2011). Autophagy facilitates glycolysis during Ras-mediated oncogenic transformation. Molecular biology of the cell 22, 165-178.

Lu, Y., Hao, B. X., Graeff, R., Wong, C. W., Wu, W. T., and Yue, J. (2013). Two pore channel 2 (TPC2) inhibits autophagosomal-lysosomal fusion by alkalinizing lysosomal pH. The Journal of biological chemistry 288, 24247-24263.

Lum, J. J., Bauer, D. E., Kong, M., Harris, M. H., Li, C., Lindsten, T., and Thompson, C. B. (2005). Growth factor regulation of autophagy and cell survival in the absence of apoptosis. Cell 120, 237-248.

Mathew, R., Karp, C. M., Beaudoin, B., Vuong, N., Chen, G., Chen, H. Y., Bray, K., Reddy, A., Bhanot, G., Gelinas, C., et al. (2009). Autophagy suppresses tumorigenesis through elimination of p62. Cell 137, 1062-1075.

Mi, S., Hu, B., Hahm, K., Luo, Y., Kam Hui, E. S., Yuan, Q., Wong, W. M., Wang, L., Su, H., Chu, T. H., et al. (2007). LINGO-1 antagonist promotes spinal cord remyelination and axonal integrity in MOG-induced experimental autoimmune encephalomyelitis. Nat Med 13, 1228-1233.

Morgan, A. J., Platt, F. M., Lloyd-Evans, E., and Galione, A. (2011). Molecular mechanisms of endolysosomal Ca2+ signalling in health and disease. The Biochemical journal 439, 349-374.

Ravikumar, B., Vacher, C., Berger, Z., Davies, J. E., Luo, S., Oroz, L. G., Scaravilli, F., Easton, D. F., Duden, R., O'Kane, C. J., et al. (2004). Inhibition of mTOR induces autophagy and reduces toxicity of polyglutamine expansions in fly and mouse models of Huntington disease. Nature genetics 36, 585-595.

Rote, K. V., and Rechsteiner, M. (1983). Degradation of microinjected proteins: effects of lysosomotropic agents and inhibitors of autophagy. Journal of cellular physiology 116, 103-110.

Rubinsztein, D. C., Codogno, P., and Levine, B. (2012). Autophagy modulation as a potential therapeutic target for diverse diseases. Nature reviews Drug discovery 11, 709-730.

Sarkar, S., Floto, R. A., Berger, Z., Imarisio, S., Cordenier, A., Pasco, M., Cook, L. J., and Rubinsztein, D. C. (2005). Lithium induces autophagy by inhibiting inositol monophosphatase. The Journal of cell biology 170, 1101-1111.

Seglen, P. O., and Gordon, P. B. (1982). 3-Methyladenine: specific inhibitor of autophagic/lysosomal protein degradation in isolated rat hepatocytes. Proceedings of the National Academy of Sciences of the United States of America 79, 1889-1892.

Shaik, G. M., Draberova, L., Heneberg, P., and Draber, P. (2009). Vacuolin-1-modulated exocytosis and cell resealing in mast cells. Cell Signal 21, 1337-1345.

Spang, A. (2009). On the fate of early endosomes. Biological chemistry 390, 753-759.

Srinivas, S. P., Ong, A., Goon, L., and Bonanno, J. A. (2002). Lysosomal Ca2+ stores in bovine corneal endothelium. Invest Ophthalmol Vis Sci 43, 2341-2350.

Wieczorek, H., Cioffi, M., Klein, U., Harvey, W. R., Schweikl, H., and Wolfersberger, M. G. (1990). Isolation of goblet cell apical membrane from tobacco hornworm midgut and purification of its vacuolar-type ATPase. Methods Enzymol 192, 608-616.

Wirawan, E., Vanden Berghe, T., Lippens, S., Agostinis, P., and Vandenabeele, P. (2012). Autophagy: for better or for worse. Cell research 22, 43-61.

Wu, Y., Wang, X., Guo, H., Zhang, B., Zhang, X. B., Shi, Z. J., and Yu, L. (2013). Synthesis and screening of 3-MA derivatives for autophagy inhibitors. Autophagy 9, 595-603.

Yamamoto, A., Tagawa, Y., Yoshimori, T., Moriyama, Y., Masaki, R., and Tashiro, Y. (1998). Bafilomycin A1 prevents maturation of autophagic vacuoles by inhibiting fusion between autophagosomes and lysosomes in rat hepatoma cell line, H-4-II-E cells. Cell structure and function 23, 33-42.

Yang, Z., and Klionsky, D. J. (2010). Eaten alive: a history of macroautophagy. Nature cell biology 12, 814-822.

Yang, Z. J., Chee, C. E., Huang, S., and Sinicrope, F. A. (2011). The role of autophagy in cancer: therapeutic implications. Molecular cancer therapeutics 10, 1533-1541.

Yue, Z., Jin, S., Yang, C., Levine, A. J., and Heintz, N. (2003). Beclin 1, an autophagy gene essential for early embryonic development, is a haploinsufficient tumor suppressor. Proceedings of the National Academy of Sciences of the United States of America 100, 15077-15082.

Zeigerer, A., Gilleron, J., Bogorad, R. L., Marsico, G., Nonaka, H., Seifert, S., Epstein-Barash, H., Kuchimanchi, S., Peng, C. G., Ruda, V. M., et al. (2012). Rab5 is necessary for the biogenesis of the endolysosomal system in vivo. Nature 485, 465-470.

We claim:

1. A method for treatment of human lung carcinoma, the method comprising administering a therapeutically effective amount of vacuolin-1 to a subject who has lung carcinoma.

2. The method according to claim 1, wherein vacuolin-1 inhibits autophagy.

3. The method according to claim 1, wherein vacuolin-1 inhibits endosomal traffic.

4. The method according to claim 1, wherein vacuolin-1 activates Rab5, which leads to maturation of endosomes and lysosomes and contributes to lysosomal pH increase.

\* \* \* \* \*

UNITED STATES PATENT AND TRADEMARK OFFICE
CERTIFICATE OF CORRECTION

PATENT NO.        : 9,717,737 B2
APPLICATION NO.   : 15/039744
DATED             : August 1, 2017
INVENTOR(S)       : Jianbo Yue and Yingying Lu It is certified that error appears in the above-identified patent and that said Letters Patent is hereby corrected as shown below:

In the Specification

Column 1,
Line 38, "Autophagyis a" should read --Autophagy is a--.

Column 3,
Line 51, "of HeLA cells" should read --of HeLa cells--.

Column 4,
Line 40, "hLCSCs. (C-F))" should read --hLCSCs. (C-F)--.
Line 45, "mice. (A). Intratumoral" should read --mice. (A) Intratumoral--.

Column 6,
Line 61, "in regular HMSS at" should read --in regular HBSS at--.
Lines 62-63, "calcium-free HMSS containing" should read --calcium-free HBSS containing--.

Column 7,
Lines 22-23, "1 μMLysosensor" should read --1 μM LysoSensor--.
Lines 33-34, "2 μM Lysosensor" should read --2μM LysoSensor--.
Line 45, "in IVIES buffer" should read --in MES buffer--.

Column 8,
Line 2, "of GST-RSBD bound" should read --of GST-R5BD bound--.
Line 4, "beads was subsequently" should read --beads were subsequently--.
Line 36, "at autophagasomes." should read --at autophagosomes.--.
Line 49, "between autophagasome and" should read --between autophagosome and--.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,717,737 B2

Column 9,
Line 15, "or homortypic fusion" should read --or homotypic fusion--.
Line 36, "ratiometricLysoSensor" should read --ratiometric LysoSensor--.
Line 40, "alkalinizes lysosomalpH." should read --alkalinizes lysosomal pH.--.

Column 11,
Lines 36-37, "chemo- and radiation therapy, thus they can survive these therapy to" should read --chemo- and radiation therapies, thus they can survive these therapies to--.
Line 61, "nasopharyngeal carcinomas cells" should read --nasopharyngeal carcinoma cells--.

Column 11, Line 67 – Column 12, Line 1,
"and 200 iL of cells was" should read --and 200 iL of cells were--.

Column 12,
Line 5, "volumes exceed 2000" should read --volumes exceeded 2000--.